United States Patent
Nordquist et al.

(10) Patent No.: US 10,682,286 B2
(45) Date of Patent: Jun. 16, 2020

(54) GASTRIC SYSTEMS, APPARATUS, AND METHODS FOR USE WITH ENTERAL FEEDING

(71) Applicant: Avent, Inc., Alpharetta, GA (US)

(72) Inventors: Jeffrey S. Nordquist, Lake Barrington, IL (US); Robert D. McVey, Arlington Heights, IL (US); Elizabeth J. Klodd, Lincolnwood, IL (US); Jon W. Newland, San Diego, CA (US); Crystal E. Koelper, North Barrington, IL (US); Jill F. Lazar, Highland Park, IL (US); Renee M. Seeler, St. Peters, MO (US); Karin A. Rogers, Collegeville, PA (US); Steven M. Maraone, Chicago, IL (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 16/218,933

(22) Filed: Dec. 13, 2018

(65) Prior Publication Data
US 2019/0110957 A1 Apr. 18, 2019

Related U.S. Application Data

(62) Division of application No. 14/846,018, filed on Sep. 4, 2015, now Pat. No. 10,188,586.
(Continued)

(51) Int. Cl.
*A61J 15/00* (2006.01)
*A61M 5/14* (2006.01)
(Continued)

(52) U.S. Cl.
CPC ....... *A61J 15/0003* (2013.01); *A61J 15/0096* (2013.01); *A61M 5/142* (2013.01);
(Continued)

(58) Field of Classification Search
CPC ...... A61J 15/0003; A61J 15/0061; A61J 1/10; A61J 15/0092; A61J 15/0096;
(Continued)

(56) References Cited

U.S. PATENT DOCUMENTS 4,240,408 A * 12/1980 Schael .................... A61M 1/28
 210/929
4,560,378 A    12/1985 Weiland
(Continued)

FOREIGN PATENT DOCUMENTS

FR    2780192 A1    12/1999
WO    WO 92/17150    10/1992
(Continued)

OTHER PUBLICATIONS

Martindale et al., "Guidelines for the provision and assessment of nutrition support therapy in the adult critically ill patient: Society of Critical Care Medicine and American Society for Parenteral and Enteral Nutrition: Executive Summary," Crit. Care Med., 2009, vol. 37, No. 5, pp. 1757-1761.
(Continued)

*Primary Examiner* — Amber R Stiles
(74) *Attorney, Agent, or Firm* — Dority & Manning, P.A.

(57) ABSTRACT

Systems, methods, and apparatus for gastric pressure relief, flow regulation, location, gastric residual volume, a placement reminder, bidirectional fluid flow markings, reintroducing gastric material, collection reservoir raising, collection reservoir hanging, a drain port, setting tube length, and vent membranes. A gastric pressure relief system is used in connection with an enteral feeding system, which includes a feeding container, administration tubing and a delivery tube, where the gastric pressure relief system is interposed between the administration tubing and the delivery tube. The gastric pressure relief system includes a collection reservoir
(Continued)

with a gas vent to ambient atmosphere, relief tubing secured to both the collection reservoir and a multi-way connector. The multi-way connector joins the administration tubing to the relief tubing and a delivery tube at a point below a patient's stomach, which is designated on a placement reminder apparatus.

13 Claims, 19 Drawing Sheets

Related U.S. Application Data

(60) Provisional application No. 62/126,241, filed on Feb. 27, 2015, provisional application No. 62/045,940, filed on Sep. 4, 2014.

(51) Int. Cl.
| | | |
|---|---|---|
| *A61M 5/142* | (2006.01) | |
| *A61M 39/22* | (2006.01) | |
| *A61M 39/24* | (2006.01) | |
| *A61M 39/08* | (2006.01) | |
| *A61M 39/10* | (2006.01) | |
| *A61J 1/10* | (2006.01) | |

(52) U.S. Cl.
CPC ........ *A61M 5/1415* (2013.01); *A61M 5/1418* (2013.01); *A61M 39/08* (2013.01); *A61M 39/10* (2013.01); *A61M 39/223* (2013.01); *A61M 39/24* (2013.01); *A61J 1/10* (2013.01); *A61J 15/0015* (2013.01); *A61J 15/0061* (2013.01); *A61J 15/0076* (2015.05); *A61J 15/0092* (2013.01); *A61J 2200/76* (2013.01); *A61M 2039/085* (2013.01); *A61M 2039/229* (2013.01); *A61M 2205/6081* (2013.01)

(58) Field of Classification Search
CPC ................ A61J 15/0015; A61J 2200/76; A61J 15/0076; A61M 39/08; A61M 39/10; A61M 2039/085
See application file for complete search history.

(56) References Cited

U.S. PATENT DOCUMENTS

| | | | |
|---|---|---|---|
| 4,836,214 A | | 6/1989 | Sramek |
| 4,921,481 A | | 5/1990 | Danis et al. |
| 5,259,587 A | | 11/1993 | D'Alessio et al. |
| 5,971,436 A | | 10/1999 | Cox |
| 6,334,064 B1 | | 12/2001 | Fiddian-Green |
| 6,357,447 B1 | | 3/2002 | Swanson et al. |
| 6,482,170 B1 | | 11/2002 | Andersen |
| 6,536,739 B1 | | 3/2003 | Jensen |
| 7,818,155 B2 | | 10/2010 | Stuebe et al. |
| 8,147,486 B2 | | 4/2012 | Honour et al. |
| 8,529,471 B2 | | 9/2013 | Holte |
| 8,613,702 B2 | | 12/2013 | Feer et al. |
| 8,900,652 B1 | | 12/2014 | Caballero et al. |
| 8,986,230 B2 | | 3/2015 | Nishtala |
| 9,179,971 B2 | | 11/2015 | Kirschenman |
| 9,226,878 B2 | | 1/2016 | Elia et al. |
| 9,295,395 B2 | | 3/2016 | Elia et al. |
| 9,532,739 B2 | | 1/2017 | Bennett-Guerrero |
| 9,610,227 B2 | | 4/2017 | Elia |
| 9,642,779 B2 | | 5/2017 | Elia et al. |
| 9,713,579 B2 | | 7/2017 | Elia et al. |
| 2002/0103066 A1 | | 8/2002 | Ostrovsky |
| 2003/0106969 A1 | * | 6/2003 | Dillon ................ A61M 5/1415 |
| | | | 248/157 |
| 2004/0054350 A1 | | 3/2004 | Shaughnessy et al. |
| 2004/0068902 A1 | | 4/2004 | Hadzic et al. |
| 2005/0000844 A1 | * | 1/2005 | Schweikert ......... A61M 39/284 |
| | | | 206/459.5 |
| 2008/0097179 A1 | | 4/2008 | Russo |
| 2008/0167607 A1 | | 7/2008 | Pfeiffer et al. |
| 2008/0249467 A1 | | 10/2008 | Burnett et al. |
| 2010/0137746 A1 | * | 6/2010 | Holte ..................... A61B 5/107 |
| | | | 600/584 |
| 2010/0280459 A1 | | 11/2010 | Werner |
| 2010/0318024 A1 | * | 12/2010 | Makowski ............ A61J 1/1475 |
| | | | 604/77 |
| 2011/0087193 A1 | | 4/2011 | Hyun |
| 2011/0275988 A1 | | 11/2011 | Davis et al. |
| 2012/0016256 A1 | | 1/2012 | Mabary et al. |
| 2012/0150111 A1 | * | 6/2012 | Hershey ................ A61M 39/08 |
| | | | 604/122 |
| 2012/0150112 A1 | | 6/2012 | Hershey et al. |
| 2012/0277619 A1 | | 11/2012 | Starkebaum et al. |
| 2012/0283627 A1 | * | 11/2012 | Moss .................. A61M 1/0058 |
| | | | 604/28 |
| 2013/0225946 A1 | | 8/2013 | Feer et al. |
| 2016/0113843 A1 | | 4/2016 | Elia et al. |
| 2016/0129223 A1 | | 5/2016 | Kirschenman |
| 2016/0331298 A1 | | 11/2016 | Burnett et al. |
| 2017/0071502 A1 | | 3/2017 | Bennett-Guerrero |
| 2017/0202750 A1 | | 7/2017 | Elia |
| 2018/0078195 A1 | | 3/2018 | Sutaria et al. |
| 2018/0161249 A1 | | 6/2018 | Elia et al. |
| 2018/0289536 A1 | | 10/2018 | Burnett |

FOREIGN PATENT DOCUMENTS

| | | |
|---|---|---|
| WO | WO 98/36789 A | 8/1998 |
| WO | WO 02/092152 A1 | 11/2002 |
| WO | WO 2013/059571 | 4/2013 |

OTHER PUBLICATIONS

Van Stappen et al., "Validation of a novel method for measuring intra-abdominal pressure and gastric residual volume in critically ill patients", Anesthesiology Intensive Therapy, 2014, vol. 46, No. 4, pp. 245-254.
Holtech Medical, Jun. 25, 2015, obtained from www.holtech-medical.com (2 pages).
Gastro PV, obtained from www.holtech-medical.com (1 page).
International Search Report and Written Opinion issued in international application No. PCT/US2015/048586, dated Apr. 7, 2016, 21 pages.

* cited by examiner

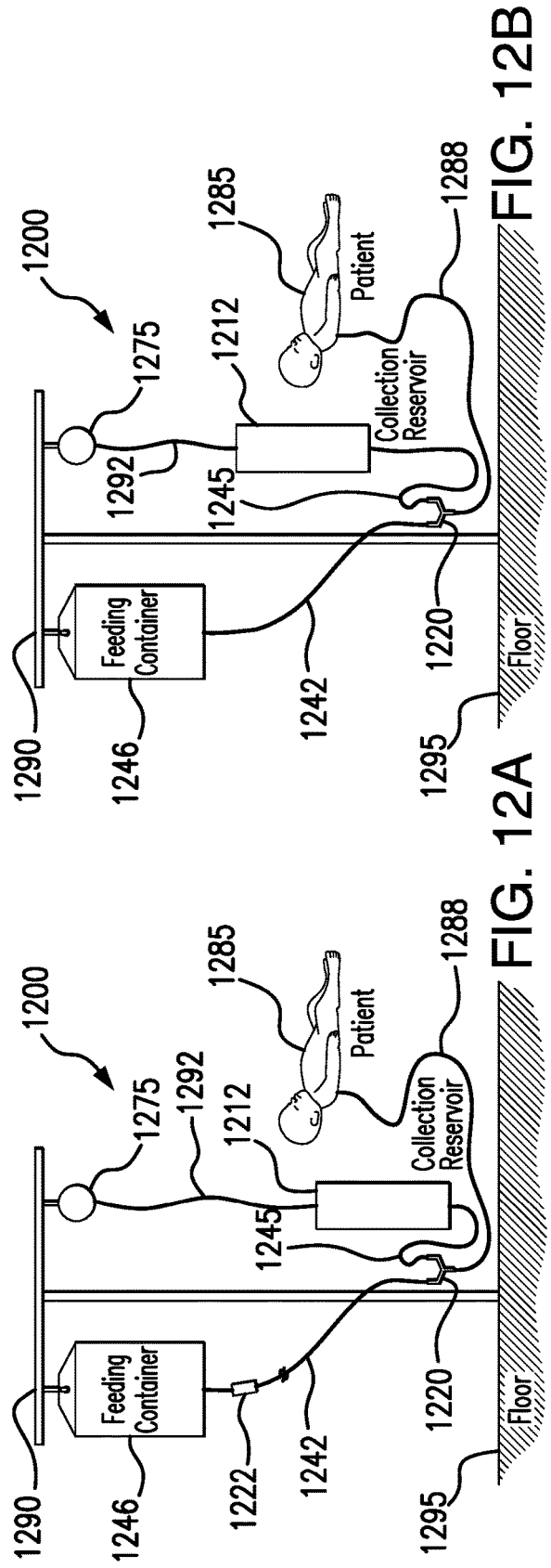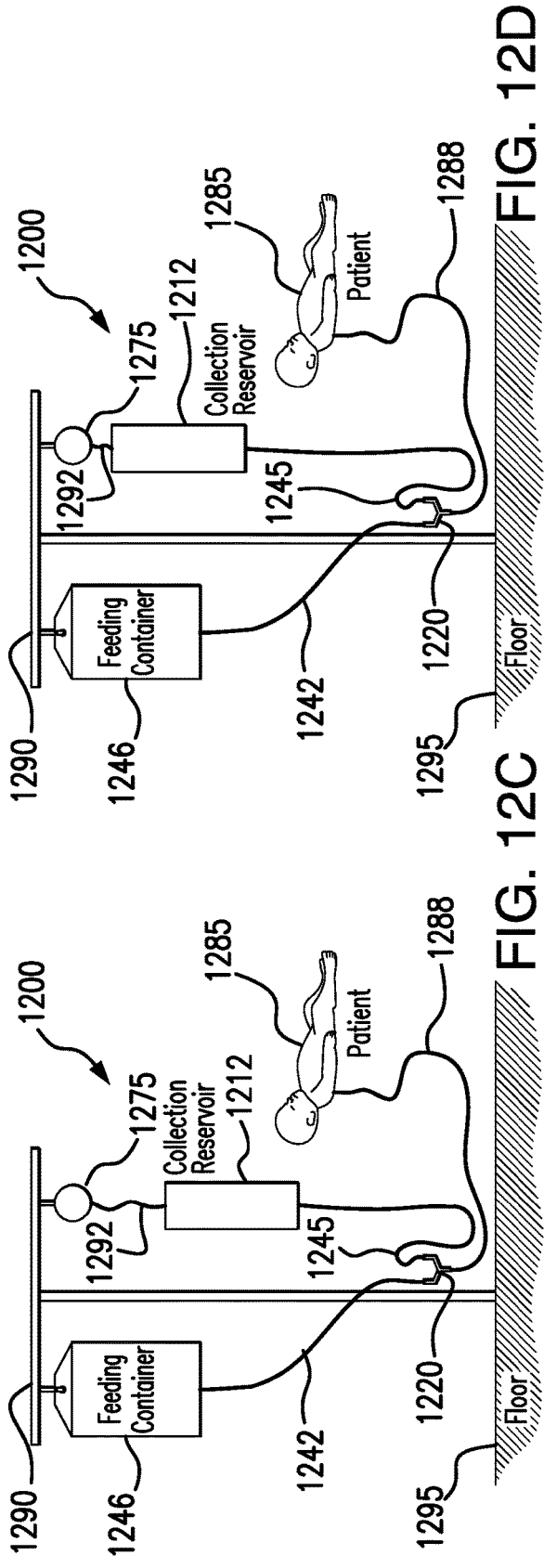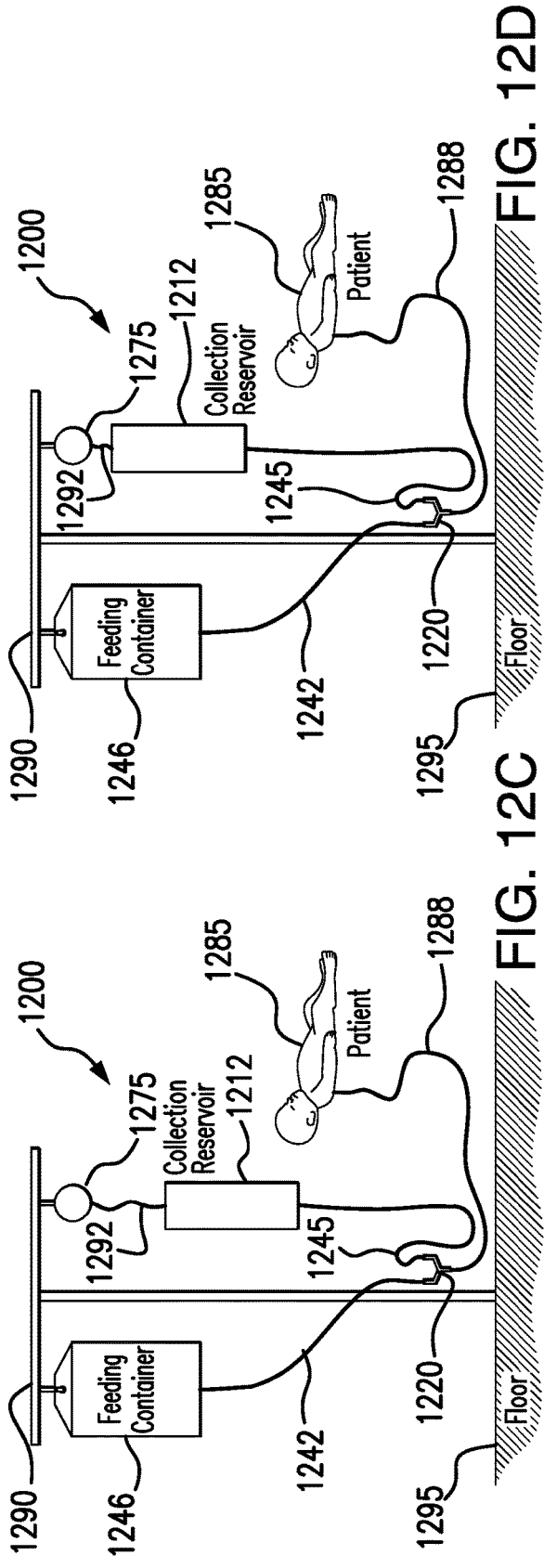

GASTRIC SYSTEMS, APPARATUS, AND METHODS FOR USE WITH ENTERAL FEEDING

PRIORITY CLAIM AND CROSS-REFERENCE TO RELATED APPLICATIONS

The present application is a divisional of U.S. application Ser. No. 14/846,018, filed Sep. 4, 2015, which claims priority to and the benefit of U.S. Provisional Patent Application Ser. No. 62/045,940, filed Sep. 4, 2014, and U.S. Provisional Patent Application Ser. No. 62/126,241, filed Feb. 27, 2015, the entire content of each of which are hereby incorporated by reference herein.

TECHNICAL FIELD

The present disclosure generally relates to enteral nutrition where fluid nutrients and/or oral medications are administered to the human gastrointestinal tract through an enteral feeding tube. For example, the present disclosure relates to systems, apparatus, and methods for relieving gastric pressure and enteral feeding intolerance during enteral feeding, including in cases involving neonatal, pediatric, adolescent and adult patients.

BACKGROUND

Enteral nutrition is a form of alimentation and metabolic support in which nutrient formulas or medications are delivered directly to the gastrointestinal tract, either the stomach, duodenum or jejunum. Nutrient administration is performed using an enteral feeding system that includes an enteral feeding container suspended above patient level and a length of flexible administration tubing connected to the container and connected to an in-dwelling enteral feeding tube. Fluid nutrient flows through the enteral feeding tube via either gravity feed, syringe bolus or use of an enteral feeding pump. Excessive gastric pressure can result during feeding, for example through accumulation of gas or liquid resulting from stomach contractions, movement of the patient's abdomen, crying or through normal formation of gas. Typically the body relieves such excess gastric pressure by expelling accumulated gas or liquid through a burping response. However, in enteral feeding where fluid nutrients are continually fed to the gastrointestinal tract, upward expulsion of gastric reflux materials is highly undesirable. Additionally, certain medical conditions prevent or limit the body's ability to eructate. Because gastric reflux pressure cannot overcome the greater forward fluid pressure within the enteral feeding tube, gastric pressure relief (also referred to as gastric decompression) devices have been developed to relieve gastric reflux pressure through the enteral feeding tube to avoid uncontrolled upward expulsion of reflux materials through the burping response; such devices also prevent introduction of air into any portion of the enteral feeding system, particularly the enteral feeding tube. Because refluxed fluid generally comprises nutrient formula being administered to the patient, after relief of gastric reflux pressure, the refluxed fluid nutrient can be returned to the enteral feeding tube for delivery to the patient. Loss of refluxed fluid can adversely impact accurate enteral administration of fluid nutrients and medications, particularly since a selected quantity of nutrient is administered over a given period of time. A need exists for a gastric reflux pressure relief system that collects, accurately measures and returns refluxed nutrient formula and medications to the enteral feeding tube.

Improved operation of enteral feeding and gastric pressure relief would represent a significant advancement in the art.

SUMMARY

The present disclosure is readily understood by the following detailed description in conjunction with the accompanying drawings. Embodiments of improved enteral feeding apparatus and methods include embodiments that utilize one or more reflux material reservoir configurations that provide improved measurement and viewing of reflux material levels by caregivers. Moreover, such reservoir configurations can utilize improved gravity-based self-centering hanger tabs. Where enteral feeding and accompanying gastric relief is being provided using such systems, fluid delivery tubing in some embodiments is reduced or minimized to reduce the amount of nutrient formula needed for priming the system and to improve monitoring of the system for reflux material detection by caregivers. One or more adjustable clamping mechanisms can improve control of fluid flow within the feeding and gastric pressure relief systems by implementing roller clamps, other adjustable flow restriction means or the like in some embodiments. Such adjustable clamping mechanisms can be controlled manually or automatically, where automatic control can be based on one or more characteristics of the reflux material reservoir. Bidirectional flow indicia are provided in some instances to inform users of the potential for bidirectional flow of fluids within some tubing segments. To reduce the risk of misuse or incorrect operation of the gastric pressure relief system, one or more placement reminders can be affixed to system components to alert individuals to the need to maintain one or more tubing connectors below the level of a patient's stomach.

In an exemplary aspect of the present disclosure, a gastric pressure relief system includes a feeding container connected to administration tubing, relief tubing, a delivery tube in fluid communication with the administration tubing and the relief tubing, a multi-way connector, a collection reservoir, and a flow regulator. The multi-way connector has a first arm, a second arm, and a third arm. Additionally, the first arm is connected to the relief tubing, the second arm is connected to the delivery tube, and the third arm is connected to the administration tubing. The collection reservoir is in fluid communication with the relief tubing. Additionally, the collection reservoir includes a vent configured to allow gas to pass through in both directions, the collection reservoir is configured to collect reflux fluids from a patient's stomach via the relief tubing, and the collection reservoir comprises volumetric indicia configured to represent a volume of reflux fluids received from the patient's stomach. The flow regulator adapted to regulate flow within the relief tubing.

In accordance with another exemplary aspect of the present disclosure, which may be used in combination with the preceding aspect, a location apparatus configured to be used with a gastric pressure relief system, the location apparatus being interposed between a feeding container and a delivery tube, the location apparatus having administration tubing connected to the feeding container, the location apparatus includes relief tubing, a multi-way connector, a collection reservoir, and a clip. The relief tubing is in fluid communication with the administration tubing and the delivery tube. The multi-way connector has a first arm, a second arm, and a third arm. The first arm is connected to the relief tubing, the second arm is connected to the delivery tube, and the third arm is connected to the administration tubing. The collection reservoir in fluid communication with the relief tubing. Additionally, the collection reservoir includes a vent configured to allow gas to pass through in both directions, the collection reservoir is configured to collect reflux fluids from a patient's stomach via the relief tubing, and the collection reservoir comprises volumetric indicia configured to represent a volume of reflux fluids received from the patient's stomach. The clip is configured to maintain the multi-way connector in a position at or below a patient's stomach level.

In accordance with another exemplary aspect of the present disclosure, which may be used in combination with any one or more of the preceding aspects, a gastric pressure relief system includes a feeding container, relief tubing, a delivery tube, a multi-way connector, a collection reservoir, and a check valve. The feeding container is connected to administration tubing. The delivery tube is in fluid communication with the administration tubing and the relief tubing. The multi-way connector has a first arm, a second arm, and a third arm. Additionally, the first arm is connected to the relief tubing, the second arm is connected to the delivery tube, and the third arm is connected to the administration tubing. The collection reservoir is in fluid communication with the relief tubing. The collection reservoir includes a vent configured to allow gas to pass through in both directions, and the collection reservoir is configured to collect reflux fluids from a patient's stomach via the relief tubing. The check valve is configured to permit flow in one direction from the administration tubing to either the relief tubing or the delivery tube.

In accordance with another exemplary aspect of the present disclosure, which may be used in combination with any one or more of the preceding aspects, a gastric pressure relief system includes a feeding container, relief tubing, a delivery tube, a multi-way connector, a collection reservoir, and a gastric residual volume measurement apparatus. The feeding container is connected to administration tubing. The delivery tube is in fluid communication with the administration tubing and the relief tubing. The multi-way connector has a first arm, a second arm, and a third arm. Additionally, the first arm is connected to the relief tubing, the second arm is connected to the delivery tube, and the third arm is connected to the administration tubing. The collection reservoir is in fluid communication with the relief tubing. The collection reservoir includes a vent configured to allow gas to pass through in both directions, and the collection reservoir is configured to collect reflux fluids from a patient's stomach via the relief tubing. The gastric residual volume measurement apparatus is interconnected to the relief tubing between the collection reservoir and the multi-way connector.

In accordance with another exemplary aspect of the present disclosure, which may be used in combination with any one or more of the preceding aspects, a placement reminder apparatus is configured to be used with a gastric pressure relief system, the placement reminder apparatus is also configured to be interposed between the distal end of a delivery tube and a feeding container connected to administration tubing, the placement reminder apparatus includes a multi-way connector, relief tubing, a collection reservoir, and a placement reminder. The multi-way connector is configured to connect the administration tubing to the delivery tube. The relief tubing is connected to the multi-way connector. The collection reservoir is connected to the relief tubing. Additionally, the collection reservoir is configured to collect reflux fluids from a patient's stomach via the relief tubing. The placement reminder is configured to be affixed to the gastric pressure relief system and includes information about the proper usage level of the connector relative to the level of a patient's stomach when the gastric pressure relief system is in use.

In accordance with another exemplary aspect of the present disclosure, which may be used in combination with any one or more of the preceding aspects, an apparatus for relieving gastric pressure during enteral feeding, the apparatus is interposed between an enteral feeding tube and an administration tubing segment connected to a fluid nutrient source, the apparatus includes a fluid delivery tube, a connector, relief tubing, a collection reservoir; and bidirectional flow markings. The fluid delivery tubing is connected to the feeding tube. The connector is configured to connect the administration tubing to the fluid delivery tubing. The relief tubing is connected to the connector. Additionally, the collection reservoir is connected to the relief tubing. The collection reservoir is configured to collect reflux fluids from a patient's stomach via the relief tubing. The bidirectional fluid flow markings are included on at least one of the sections of tubing include the relief tubing, the administration tubing, and the delivery tube. The bidirectional markings are used to inform users of the gastric pressure relief system of the bidirectional flow of fluids within any tubing segment marked with the bidirectional fluid flow markings.

In accordance with another exemplary aspect of the present disclosure, which may be used in combination with any one or more of the preceding aspects, a method of reintroducing gastric material to a patient includes restricting flow of nutrients from a feeding container, initiating gradual raising of a collection reservoir from a starting position to a nominal position, wherein the starting position is below a patient's stomach level, and raising the collection reservoir in a stepwise progression to provide initial draining when the collection reservoir is in a first intermediate position, wherein raising the collection reservoir to the next stepwise progression is not performed until gastric reflux material equilibrium is achieved.

In accordance with another exemplary aspect of the present disclosure, which may be used in combination with any one or more of the preceding aspects, a collection reservoir raising apparatus includes a support stand, a collection reservoir, a delivery tube, and a connector. The collection reservoir is in fluid communication with relief tubing. Additionally, the collection reservoir includes a vent configured to allow gas to pass through in both directions, and the collection reservoir is configured to collect reflux fluids from a patient's stomach via the relief tubing. The connector is in fluid communication with the relief tubing and the delivery tube. The pulley is connected to the support stand, and the cord connected to the collection reservoir, wherein the cord is configured to fit through the pulley and raise the collection reservoir.

In accordance with another exemplary aspect of the present disclosure, which may be used in combination with any one or more of the preceding aspects, a collection reservoir can be used in connection with an enteral feeding system that includes relief tubing, a connector, and a delivery tube. The collection reservoir includes at least two chambers configured to receive gastric reflux materials from an enteral feeding system relief tubing.

In accordance with another exemplary aspect of the present disclosure, which may be used in combination with any one or more of the preceding aspects, a collection reservoir for use in connection with an enteral feeding system including relief tubing, a connector, and a delivery tube, the collection reservoir includes a frusto-conical chamber configured to receive gastric reflux materials from enteral feeding system gastric pressure relief tubing. The frusto-conical chamber is defined by a wall comprised of either a rigid material or a pliable material. The wall further includes volumetric indicia configured to represent a volume of reflux material received from the enteral feeding system.

In accordance with another exemplary aspect of the present disclosure, which may be used in combination with any one or more of the preceding aspects, collection reservoir hanging apparatus for use with a gastric pressure relief system includes a feeding container, relief tubing, a delivery tube, a multi-way connector, and a collection reservoir. The feeding container is connected to administration tubing. The delivery tube is in fluid communication with the administration tubing and the relief tubing. The multi-way connector has a first arm, a second arm, and a third arm. Additionally, the first arm is connected to the relief tubing, the second arm is connected to the delivery tube, and the third arm is connected to the administration tubing. The collection reservoir is in fluid communication with the relief tubing. The collection reservoir includes a vent configured to allow gas to pass through in both directions. The collection reservoir is configured to collect reflux fluids from a patient's stomach via the relief tubing. The collection reservoir includes a hanger tab with a self-centering aperture, and the collection reservoir includes volumetric indicia configured to represent a volume of reflux fluids received from the patient's stomach.

In accordance with another exemplary aspect of the present disclosure, which may be used in combination with any one or more of the preceding aspects, a gastric pressure relief system includes a feeding container connected to administration tubing, relief tubing, a delivery tube, a multi-way connector, a collection reservoir, and a drain port. The delivery tube is in fluid communication with the administration tubing and the relief tubing. The multi-way connector having a first arm, a second arm, and a third arm. Additionally, the first arm is connected to the relief tubing, the second arm is connected to the delivery tube, and the third arm is connected to the administration tubing. The collection reservoir is in fluid communication with the relief tubing. Additionally, the collection reservoir includes a vent configured to allow gas to pass through in both directions, the collection reservoir is configured to collect reflux fluids from a patient's stomach via the relief tubing, and the collection reservoir includes volumetric indicia configured to represent a volume of reflux fluids received from the patient's stomach. The drain port connected to the collection reservoir.

In accordance with another exemplary aspect of the present disclosure, which may be used in combination with any one or more of the preceding aspects, an apparatus for relieving gastric pressure during enteral feeding, the apparatus is interposed between a feeding tube and administration tubing connected to a feeding container. The apparatus includes a multi-way connector, a fluid delivery tube, relief tubing, and a collection reservoir. The fluid delivery tubing is connected to the feeding tube. The multi-way connector is configured to connect the administration tubing to the fluid delivery tubing. The fluid delivery tubing has a first length defined by the minimum length required to position the multi-way connector at a patient stomach level when the feeding tube is providing fluid nutrient to a patient. The relief tubing is connected to the multi-way connector. The collection reservoir is connected to the relief tubing, and the collection reservoir is configured to collect reflux fluids from a patient's stomach via the relief tubing.

In accordance with another exemplary aspect of the present disclosure, which may be used in combination with any one or more of the preceding aspects, a method for providing gastric pressure relief during enteral feeding, wherein the enteral feeding is implemented using a feeding container that delivers fluid nutrient to a feeding tube via administration tubing, and a gastric pressure relief system is interposed between the administration tubing and the feeding tube. The method includes intubating the feeding tube in a patient, measuring the approximate shortest distance between the feeding tube proximal end and a vertical plane at the level of the patient's stomach, setting the length of the fluid delivery tubing segment to approximately the measured shortest distance, coupling the fluid delivery tubing to the feeding tube and to a multi-way connector, and providing fluid nutrient to the patient. The feeding tube has a proximal end outside the patient's body.

In accordance with another exemplary aspect of the present disclosure, which may be used in combination with any one or more of the preceding aspects, a gastric pressure relief system includes a feeding container, relief tubing, a delivery tube, a multi-way connector, and a collection reservoir. The feeding container is connected to administration tubing. The delivery tube is in fluid communication with the administration tubing and the relief tubing. The multi-way connector has a first arm, a second arm, and a third arm. Additionally, the first arm is connected to the relief tubing, the second arm is connected to the delivery tube, and the third arm is connected to the administration tubing. The collection reservoir in fluid communication with the relief tubing. Additionally, the collection reservoir includes a vent that is configured to allow gas to pass through in both directions. The vent includes one or more membranes configured to restrict the flow of liquid through the vent, and the collection reservoir is configured to collect reflux fluids from a patient's stomach via the relief tubing.

Additional features and advantages of the disclosed system, method, and apparatus are described in, and will be apparent from, the following Detailed Description and the Figures.

BRIEF DESCRIPTION OF THE FIGURES

FIGS. 12A-12D illustrate one or more example embodiments of a reservoir-raising method implementable with enteral feeding and gastric pressure relief systems and the like, according to an example embodiment of the present disclosure.

DETAILED DESCRIPTION OF EXAMPLE EMBODIMENTS

Figure 1:
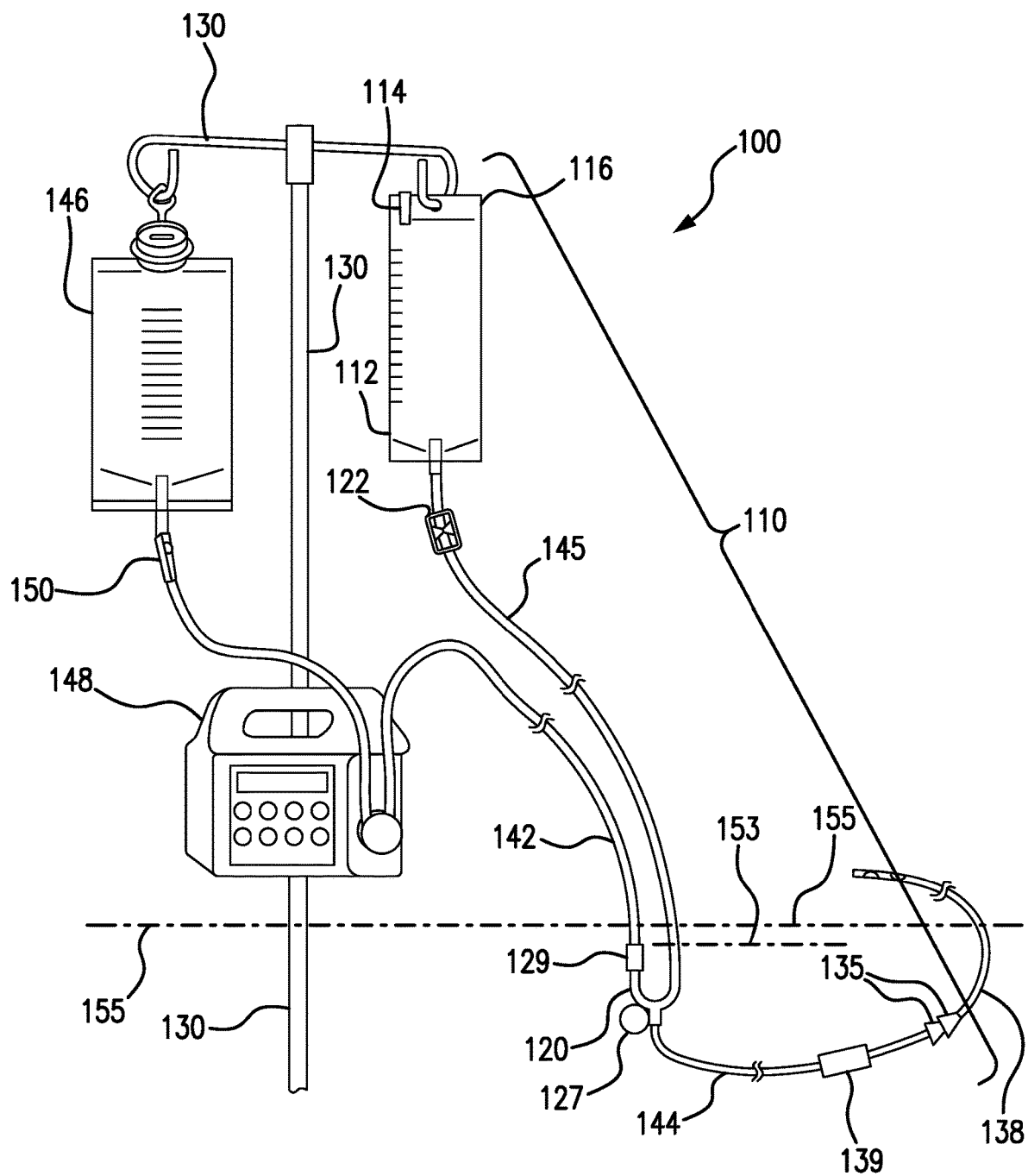
FIG. 1 illustrates a perspective view of a gastric pressure relief device implemented in connection with an enteral feeding system, according to an example embodiment of the present disclosure.

Referring to the Figures, embodiments of an enteral feeding and gastric pressure relief/suction device are disclosed. As seen in the exemplary enteral feeding system 100 illustrated in FIG. 1, an enteral feeding container 146 containing a selected nutrient formula is suspended from support stand 130. Other enteral feeding system arrangements and configurations can be used in connection with the embodiments of the disclosure illustrated and discussed herein, as will be appreciated by those skilled in the art. The flow rate for delivery of nutrient formula from enteral feeding container 146 through administration tubing 142 may be accomplished through use of an enteral feeding pump 148 in combination with use of an administration tube set clamp 150. Nutrient formula flow rate may also be achieved through gravity feed controlled through the combination of a drip chamber and a tubing clamp (e.g., a roller or other adjustable clamp).

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Also, it should be appreciated that the features of the dependent claims may be embodied in the systems, methods, and apparatus of each of the independent claims.

The term "fluid" as used herein refers to and includes both gas and liquid physical states. Referring to the Figures, embodiments of a gastric pressure relief (also referred to as gastric decompression) device are disclosed. As explained in greater detail below, gastric pressure relief system 110 of FIG. 1 is interposed between and connects enteral administration tubing 142 to an enteral feeding tube 138 (e.g., a nasioenteric tube, orogastric trube, gastrostomy tube, or the like). Gastric pressure relief system 110 is connected to the feeding tube 138 using a connector apparatus 135, which can be a standard enteral feeding connector apparatus. Gastric pressure relief system 110 generally comprises a reflux material collection reservoir 112 which, as explained in more detail below, is configured to receive materials (i.e., gas and/or liquid) refluxed from a patient's stomach during gastric pressure relief. In FIG. 1, collection reservoir 112 is vented to the ambient atmosphere through a gas vent 114 and is suspended from support stand 130 by a hanger tab 116. A segment of relief tubing 145 connects collection reservoir 112 to a connector, such as a Y-connector 120; a relief tubing clamping mechanism 122 can be used to selectively control the flow of gases and liquids between Y-connector 120 and collection reservoir 112. Fluid delivery tubing 144 and administration tubing 142 also are connected to Y-connector 120, and a nutrient supply line clamping mechanism 139 can be used selectively to prevent flow between the Y-connector 120 and the feeding tube 138.

Gastric pressure relief system 110 as illustrated in FIG. 1 comprises collection reservoir 112, which is vented to ambient atmospheric pressure. To avoid introducing air into the enteral feeding tube 138 through relief tubing 145 and fluid delivery tubing 144, gastric pressure relief system 110 is configured to provide a small column of liquid (e.g., nutrient formula or other liquid) in relief tubing 145. This is accomplished by properly positioning Y-connector 120 at or slightly below the level of a patient's stomach. For reference and illustrative purposes, the patient's stomach level is indicated in FIG. 1 by line 155. So long as Y-connector 120 is at or below that patient stomach level 155 (or, e.g., the patient's mid-axillary line), a small column of liquid (e.g., nutrient formula or other liquid) enters and remains suspended in relief tubing 145 with the meniscus of the column generally at line 153 in FIG. 1 (in close proximity to, or at the same level as the stomach level 155, typically based on the physical condition of the patient). This fluid column prevents air from being drawn into fluid delivery tubing 144 and, ultimately, into enteral feeding tube 138.

Preferably, Y-connector 120 is a Y-shaped connector, although other multi-way connectors known or used in the art are suitable so long as fluid communication between administration tubing 142, fluid delivery tubing 144 and relief tubing 145 is maintained. Fluid delivery tubing 144 receives nutrient formula from administration tubing 142 via Y-connector 120 and delivers such nutrient formula to the enteral feeding tube 138. In addition, in conditions of excessive gastric pressure, fluid delivery tubing 144 passes reflux materials (gas and/or liquid) in the opposite direction, through Y-connector 120 into pressure relief tubing 145 (and, if necessary, into collection reservoir 112). Any reflux gas that passes through fluid delivery tubing 144 is channeled into relief tubing 145, passing upward through collection reservoir 112, through gas vent 114 and into the ambient atmosphere.

In some embodiments additional apparatus and/or measures can be taken to maintain Y-connector 120 at or below the level of the stomach of a user or patient, and additionally help with tubing management (e.g. avoiding tangling, avoiding interfering with patient's sleep, ambulatory activities, and the like).

For example, a clip 127 (e.g., a clothing clip) or other connecting means can be incorporated as part of or be adapted to hold Y-connector 120 securely to clothing, pajamas, or bed linens, as seen in FIG. 1. Clip 127 assists in maintaining placement of the Y-connector 120. In another embodiment, the connecting means can be a hydrocolloid or other suitable adhesive that adheres directly to the patient's skin to maintain placement of Y-connector 120. In some embodiments a heavier construction material is used for Y-connector 120 or a weight is placed or affixed to Y-connector 120 to assist in its maintaining placement at or below the level of the patient's stomach. Accordingly, the enteral feeding system 100/gastric pressure relief system 110 is provided with a location apparatus to advantageously maintain the location of the Y-connector 120.

Additionally, a one-way check valve 129 or other backflow prevention means can be integrated into enteral feeding system 100 to prevent retrograde flow back into administration tubing 142 (and thus into feeding container 146). One-way check valve 129 can be an internal valve in one arm of Y-connector 120, or it can be interposed between Y-connector 120 and administration tubing segment 142. One-way check valve 129 permits flow only in one direction (i.e., toward relief tubing 145 and/or fluid delivery tubing 144) and can be used, for example, when an enteral feeding system is operated in "gravity mode" (i.e., without a fluid pump or the like).

As noted above with regard to the exemplary configuration of FIG. 1, Y-connector 120 defines and permits fluid communication between (a) relief tubing 145 seated within a first arm of Y-connector 120, (b) fluid delivery tubing 144 seated within a second arm of Y-connector 120, and (c) administration tubing 142 seated within the third arm of Y-connector 120.

In a forward feeding flow configuration, nutrient formula or the like flows from the feeding container 146 through the administration tubing 142 through the third arm of Y-connector 120. Then, the fluid passes through the bottom or second arm of the Y-connector 120 to the fluid delivery tubing 144 through connector apparatus 135 and into feeding tube 138. As discussed herein, a delivery tube may be a combination of the fluid delivery tubing 144 and the feeding tube 138, or the delivery tube may be a single component which delivers fluid and feeds the patient, such that a connector apparatus 135 is not required. The delivery tube has a proximal end and a distal end, and the proximal end of the delivery tube is connected to the second arm of the Y-connector 120. Additionally, in a reverse collection configuration, gastric material or the like travels through feeding tube 138 through connector apparatus 135 and into the fluid delivery tubing 144. From the fluid delivery tubing 144, the gastric material passes through the second arm of Y-connector 120 through the first arm of Y-connector 120 and into relief tubing 145. Then, the gastric material enters collection reservoir 112. The relief tubing 145 is interposed between a distal end of the fluid delivery tubing 144 and the feeding container 146, or between the distal end of the delivery tube and the feeding container 146. Similarly, when gastric material is returned to the patient, the gastric material flows from collection reservoir 112, through relief tubing 145 and into the first arm of Y-connector 120. Then, the fluid flows through the second arm of Y-connector 120 into fluid delivery tubing 144, through connector apparatus 135, into feeding tube 138.

Figure 2A:
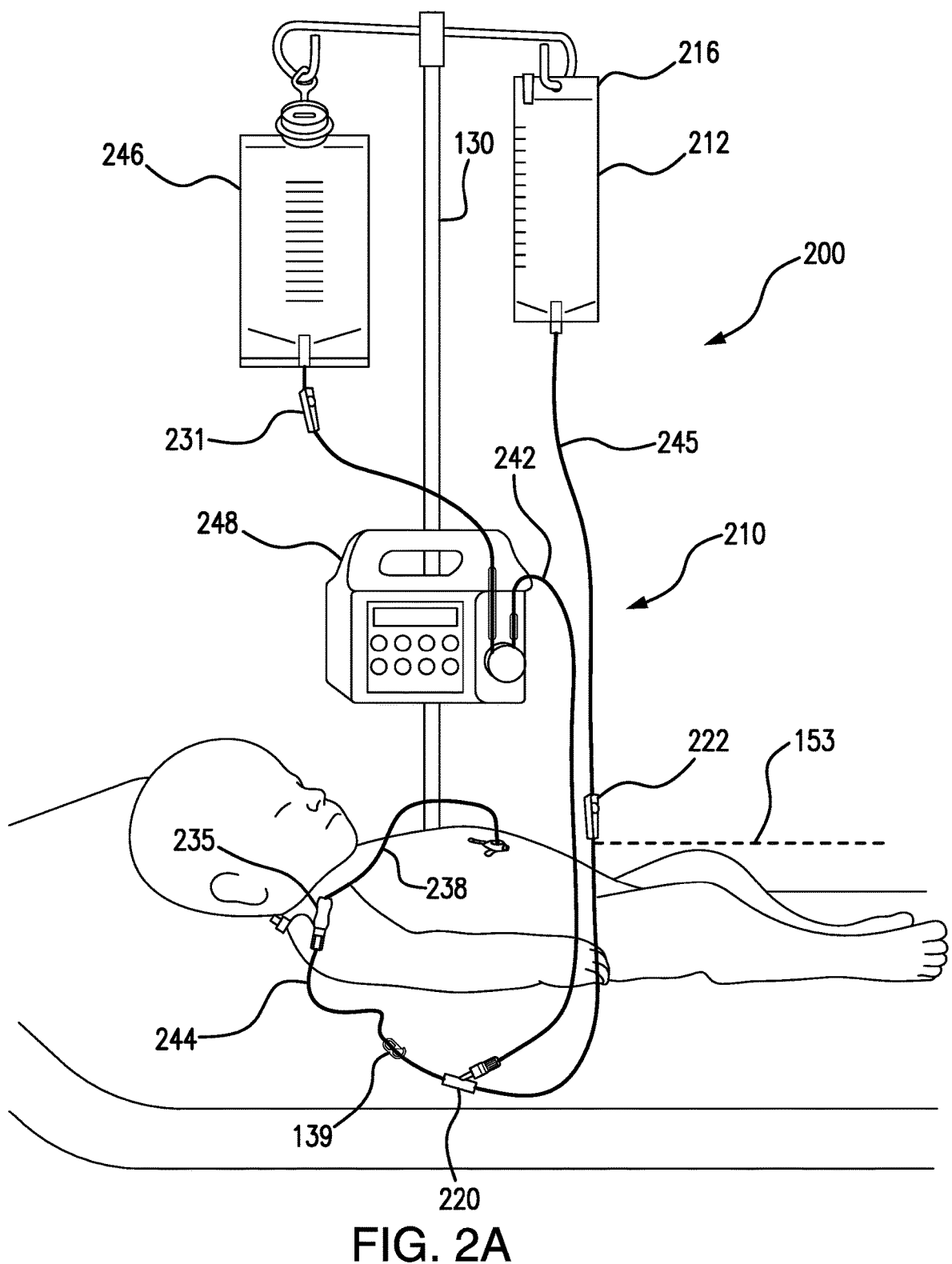
FIGS. 2A-2C illustrate perspective views of gastric pressure relief devices implemented in connection with an enteral feeding system employed in caring for neonate, infants and the like, which can also be adapted to use in connection with adolescents, adults and other patients, according to an example embodiment of the present disclosure.

Some gastric pressure relief system embodiments are configured to treat neonatal, infant and other, similar patients (e.g., in a NICU setting or the like) and to minimize and/or substantially reduce the length of tubing incorporated in the gastric pressure relief system, for example, the tubing required between a gastric pressure relief system connector and the patient. FIGS. 2A though 2C illustrate several exemplary scenarios for enteral feeding of a neonate, infant or other small child. In FIG. 2A, a child is shown being fed with a gastrostomy tube feeding system 200 in which the feeding tube 238 provides nutrient liquid through a stoma in the patient's abdomen. Fluid delivery tubing 244 connects feeding tube 238 to a gastric pressure relief system 210 that also includes a Y-connector 220 to which administration tubing 242 and relief tubing 245 also are connected. Administration tubing 242 delivers nutrient formula or the like from a feeding container 246 via pump 248, gravity, etc. A roller clamp or other clamping mechanism 231 can be used to assist in regulating nutrient flow from feeding container 246. Relief tubing 245 connects Y-connector 220 to reservoir 212; again, a roller clamp 222 coupled to relief tubing 245 can be used to control flow between Y-connector 220 and reservoir 212. Gastric pressure relief system 210 is connected to the feeding tube 238 using a connector apparatus 235, which can be a standard enteral feeding connector apparatus.

Figure 2B:
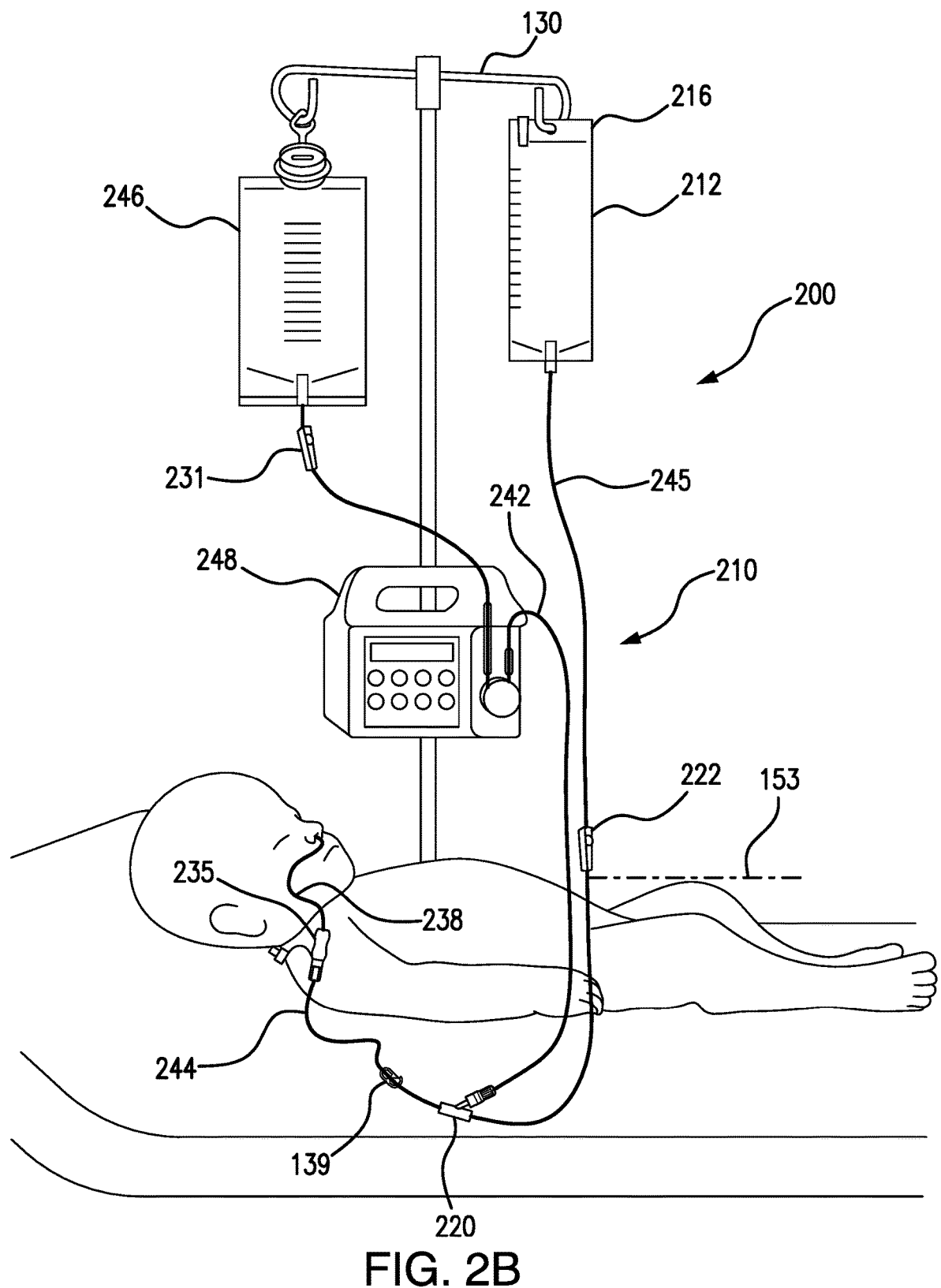
Figure 2C:
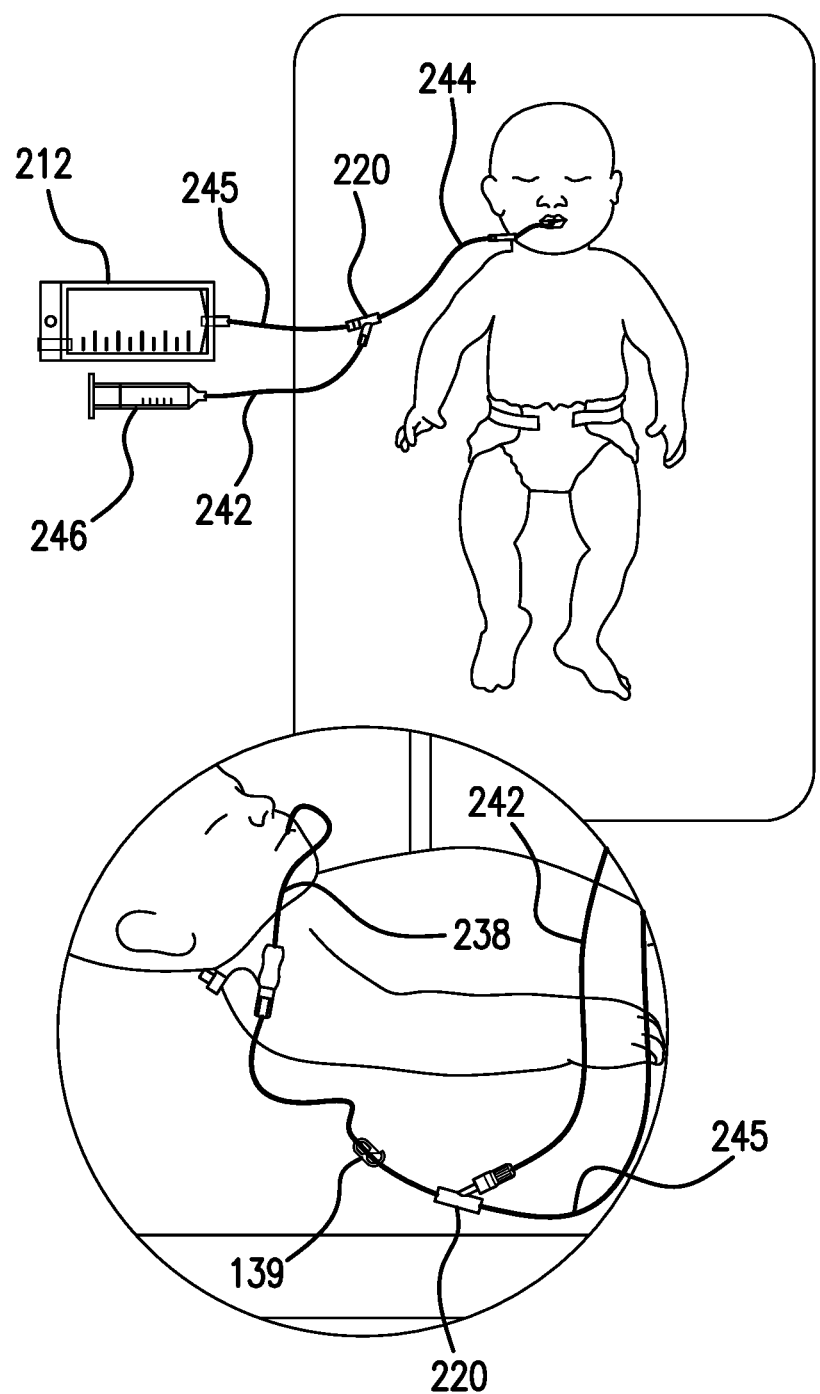

FIG. 2B similarly illustrates a comparable feeding system 200 in which the feeding tube 238 extends from the patient's nare. Feeding tube 238 is connected via connector apparatus 235 to fluid delivery tubing 244 of gastric pressure relief system 210 that also includes a Y-connector 220. Administration tubing 242 and relief tubing 245 also are connected to Y-connector 220. Administration tubing 242 delivers formula from feeding container 246 via pump 248. A roller clamp or other clamping mechanism 231 assists in regulating flow from feeding container 246. Relief tubing 245 connects Y-connector 220 to reservoir 212; again, a roller clamp 222 coupled to relief tubing 245 is used to control flow between Y-connector 220 and reservoir 212. Gastric pressure relief system 210 is connected to the feeding tube 238 using a connector apparatus 235. FIG. 2C illustrates a system in which an orogastric feeding tube 238 is used with similar feeding and gastric pressure relief systems, as explained in connection with FIGS. 2A and 2B.

In the embodiments of FIGS. 2A-2C, the Y-connector 220 must be kept at or below the patient's stomach level (as noted above, some embodiments may include one or more suitable placement reminders to that effect). However, the small size of the patient, low delivery flow rates, and the nature of some nutrient formulas used in feeding such patients (e.g., breast milk) provides a different situation than is found with larger patients. In the embodiments of FIGS. 2A through 2C, the feeding tube 238 and fluid delivery tubing 244 are sized to reduce (and in some embodiments to minimize) the length of the fluid delivery tubing 244 so that the amount of nutrient formula required to prime the gastric pressure relief system is reduced or minimized.

The minimum length of the combined feeding tube 238 and fluid delivery tubing 244 in the exemplary systems of FIGS. 2A-2C is the shortest distance between the exit point of feeding tube 238 (that is, the point where the feeding tube 238 exits the patient's body—e.g., a body orifice such as a nasal nare (for NG tubes) or a stoma when a gastric feeding tube (G-tube), jejunostomy feeding tube (J-tube), gastrojejunostomy feeding tube (GJ-tube), or percutaneous endoscopic gastrostomy tube (PEG-tube) is used) and the plane of the patient's stomach level (in some instances, that is an intersection point with the coronal (or frontal) plane located near the midaxillary line just below the stomach position relative to the anterior (ventral) portion of the abdomen and the posterior (dorsal) portion of the back).

By minimizing or substantially reducing the length of the fluid delivery tubing 244, the illustrated gastric pressure relief system embodiments substantially reduce the amount of nutrient formula required to prime the system for use. Moreover, reduced-tubing gastric pressure relief system embodiments are able to provide improved feedback to a caretaker such as a nurse when there is gastric pressure and/or reflux in a small patient because a small amount of reflux material will be more readily noticeable in the substantially shorter tubing of such reduced-tubing gastric pressure relief system embodiments.

A method for providing gastric pressure relief during enteral feeding using this reduced tubing implementation can be performed when enteral feeding is implemented using a fluid nutrient source that delivers fluid nutrient to an enteral feeding tube via administration tubing 242. A gastric pressure relief system 210 is interposed between the administration tubing 242 and the enteral feeding tube 238. The method begins with the intubation of the enteral feeding tube 238 in a patient, where the enteral feeding tube 238 has a proximal end outside the patient's body. The approximate shortest distance between the enteral feeding tube 238 proximal end and a vertical plane at the level of the patient's stomach is then either measured or estimated and the length of the fluid delivery tubing 244 is set to approximately the measured shortest distance, for example by cutting the fluid delivery tubing 244 to the proper length or selecting fluid delivery tubing 244 having a pre-measured length. The fluid delivery tubing 244 is then coupled to the enteral feeding tube 238 and to the Y-connector 220 (or other connecting means) and the fluid nutrient is then provided to the patient.

The apparatus illustrated in the Figures and methods implemented using such apparatus can be employed in various ways to assist in the feeding and care of a patient. The following disclosure of one or more modes of operation, processes, methods and the like is not limiting, but is being provided for illustrative purposes only.

Using the gastric pressure relief system 110 of FIG. 1 for explanatory purposes, the feeding container 146 is suspended from support stand 130 or the like, along with administration tubing 142 and with any other nutrient supply apparatus. The collection reservoir 112 is suspended at the same height as feeding container 146, for example also being suspended from support stand 130. Clamping mechanism 122 on relief tubing 145 is closed completely, thus preventing fluid flow between Y-connector 120 and collection reservoir 112.

Administration tubing 142 is then connected to Y-connector 120 at the same time that fluid delivery tubing 144 is primed, for example with fluid nutrient. Priming in some cases may also include priming the relief tubing 145 to a level slightly above Y-connector 120. As noted above, in some embodiments the amount of nutrient required is reduced (or minimized) by utilizing a reduced length of fluid delivery tubing 144 (and, if adjustable, feeding tube 138 as well). In some methods, a measured or approximated minimum distance between the exit point of the feeding tube 138 and the patient's stomach level can be made, after which a fluid delivery tubing length is selected (or, in some cases, the fluid delivery tubing length is reduced by cutting) based on the minimum distance measurement or approximation. The nutrient supply line clamping mechanism 139 also is closed at this time to prevent flow between the administration tubing 142 and the feeding tube 138.

The fluid delivery tubing 144 is then connected to feeding tube 138. Clamping mechanism 139 is opened (either partially or fully) to permit the flow of nutrient from feeding container 146 to the feeding tube 138 (and thus the patient). Then clamping mechanism 122 is opened (again, either partially or fully) to permit initial equilibrium to be reached in gastric pressure relief system 110 and thereafter to permit the flow of reflux materials through the fluid delivery tubing 144 and Y-connector 120 to relief tubing 145 and, if needed, collection reservoir 112 (which can be one of any of the embodiments of the present disclosure). The normal height of formula in the relief tubing 145 will typically be slightly above the patient's stomach level. Patients on very low volume feeding (e.g., neonates) may require substantially longer time to establish nutrient flow before opening clamping mechanism 122, or before opening clamping mechanism 122 completely. The fluid level within relief tubing 145 and collection reservoir 112 may move up and down continuously and/or frequently.

Clamping Mechanism and Control

A clamping mechanism 122 can be carried on relief segment 145. In some embodiments, clamping mechanism 122 is a roller clamp 222 that can be used to selectively and adjustably prevent, limit and/or meter the rate of flow of contents between collection reservoir 112 and a patient (e.g., to avoid further expulsion or overfeeding, to slow the rate of return of reservoir contents to the patient, etc.). In some roller clamp embodiments, to adjust fluid (i.e., liquid and gas) flow through tubes such as relief tubing 145, the tube is held in a channeled holder and a wheel or the like mounted between opposite side walls of the holder applies adjustable pressure (e.g., deforming or pinching pressure) on the tube that is dependent on the wheel's rotary position. A ratchet wheel with a spring detent may be attached to the wheel for rotating it and positively locking it in a desired position. In addition to the variable clamping mechanism (e.g., a roller clamp 222) settings, the roller clamp 222 can also be adjusted to be completely open or completely closed, assisting with the device's setup.

In other embodiments the clamping mechanism 122 of FIG. 1 can be a binary on/off style clamp. In the various embodiments, clamping mechanism 122 can close relief tubing 145 completely, causing gastric pressure relief system 110 to become inoperative.

Figure 3A:
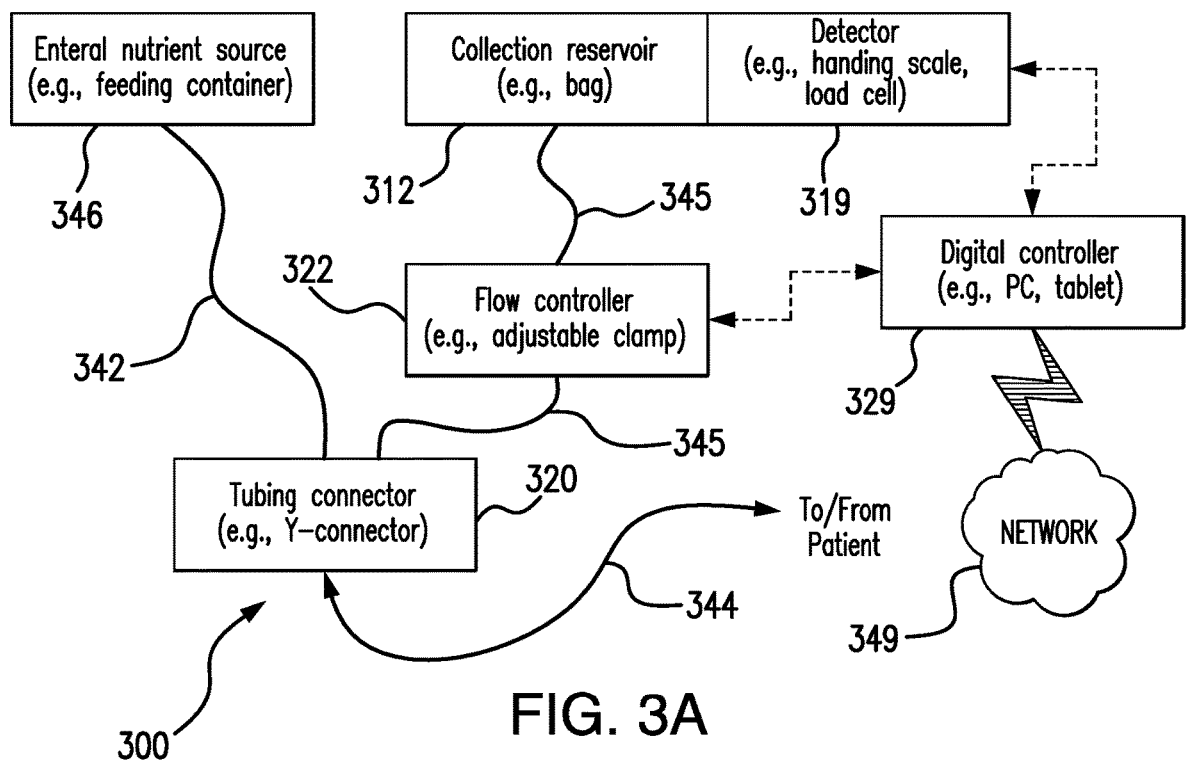
FIG. 3A shows a block diagram of one or more embodiments in which flow control to and from a reflux material reservoir is regulated automatically, according to an example embodiment of the present disclosure.
Figure 3B:
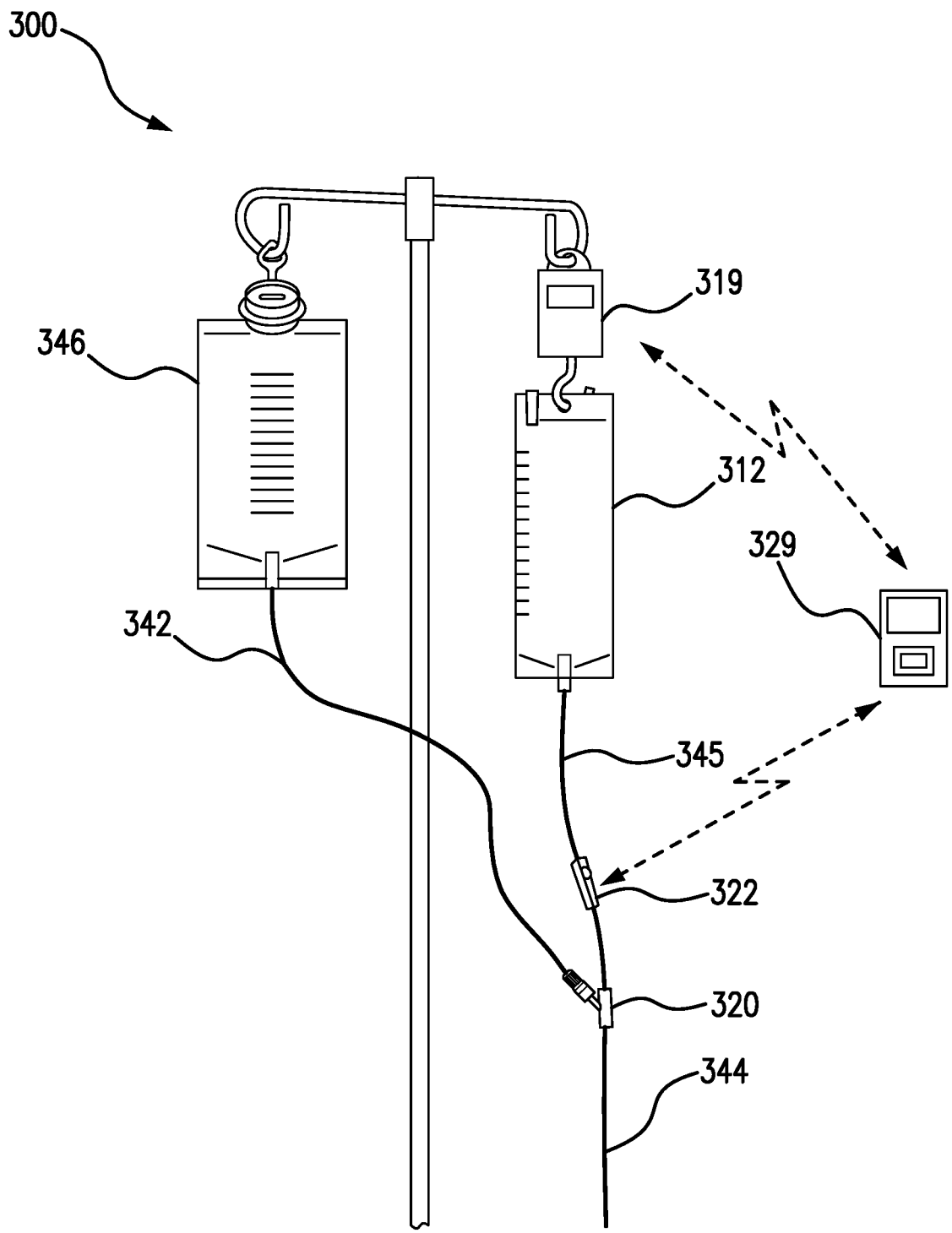
FIG. 3B illustrates a perspective view of a gastric pressure relief device with automatic flow control regulation, according to an example embodiment of the present disclosure.

A roller clamp 222 or other adjustable clamping mechanism can act as a flow controller in an automated system that controls fluid flow based on one or more factors or criteria. For example, FIG. 3A is a block diagram of system 300, and corresponding FIG. 3B illustrates a perspective view of system 300, in which an enteral nutrient source 346 (e.g., an enteral feeding container) supplies nutrient formula or the like via administration tubing 342 to a tubing connector 320 such as a Y-connector 220 or the like. Connector 320 in turn supplies formula via fluid delivery tubing 344 to a patient. Reflux material can flow from the patient via fluid delivery tubing 344, through connector 320 and up to a collection reservoir 312, which also can be a bag or the like, via relief tubing 345. A flow controller 322 is configured to regulate the flow of materials to and from collection reservoir 312 and the patient. In system 300, flow controller 322 is connected to a digital controller 329, which can be a PC, a tablet, or another suitable control device. A detector 319 is coupled to collection reservoir 312 and can be configured to detect one or more physical characteristics of collection reservoir 312, for example its weight (e.g., using a hanging scale, a load cell, etc.). In other embodiments, pressure within relief tubing 345 may be measured and threshold levels detected in order to control flow controller 322. Detector 319 transmits signals (wirelessly, by BlueTooth or via wireline communication) to digital controller 329, which processes the signals to determine the setting for flow controller 322. Digital controller 329 also can communicate data to other locations (e.g., a nursing station) via a network 349.

Gastric Residual Volume Valving and Methods

Enteral feeding systems are well-suited for assisting with other aspects of patient care and/or treatment, for example measuring and adjusting feeding rates and patient gastric accumulations. Gastric residual volume ("GRV") measurement is a common practice in critical care nutrition therapy as an indicator of conditions such as feeding intolerance, the risk of aspiration (and aspiration pneumonia), and gastric emptying. GRV levels tend to be higher at initiation of enteral feeding therapy and lower as tolerance increases, intestinal contractility is restored, and the patient recovers clinically. Clinically, there is a lack of standardization in measuring GRV. Many current procedures for GRV measurement are burdensome, clumsy, messy, and unpleasant. Those that employ an "open" system (e.g., one where the patient's gastric aspirate is open to the external environment) also risk clinician and caregiver exposure to the patient's bodily fluids. Such potential exposure to patient's bodily fluids also require additional Personal Protective Equipment (PPE) per the Centers for Disease Control and Prevention (CDC) and the National Institute for Occupational Safety and Health (NIOSH). Checking GRVs using earlier methods (such as a syringe extraction and beaker collection) is also a time consuming process. Many hospital institutions assess GRV in patients 4-6 times per day (e.g., every 4-6 hours). For example, the American Society of Parenteral and Enteral Nutrition (ASPEN) recommends to check gastric residuals every 4 hours during the first 48 hours for gastrically fed patients. Also according to ASPEN, when GRV levels are greater than 250 mL, clinical interventions should be considered, and at GRV of 500 mL, enteral nutrition should be stopped. Easily assessing and monitoring GRV is therefore extremely beneficial clinically. Once collected or retained, it is important to return the gastric aspirate to the patient as it contains essential gastric contents that are important for normal gastro intestinal tract function, protection, and digestion. Return of gastric aspirate also ensures that the patient is receiving all prescribed nutrients (e.g., calories, electrolytes, etc.) and medications.

Previous GRV measurement apparatus and methods have depended upon a "passive GRV measurement" approach, in which a bag or other container is lowered to a level below the height of a patient's stomach, mid-axillary line or other anatomical marker and gravity thereafter acts to drain (siphon) a patient's gastric contents into the container. The container's contents are measured and can then be disposed of, returned to the patient's stomach "passively" (i.e., flowing from a container situated above the anatomical marker and allowing gravity to move the container's contents from the container to the patient's stomach), or a combination of the two. In the embodiments disclosed herein, passive GRV measurement will be distinguished from "active" GRV measurement—in active GRV measurement, a manmade force is applied to move gastric contents within a given enteral feeding system or the like. Several embodiments of apparatus for performing this active GRV measurement are described.

Figure 4:
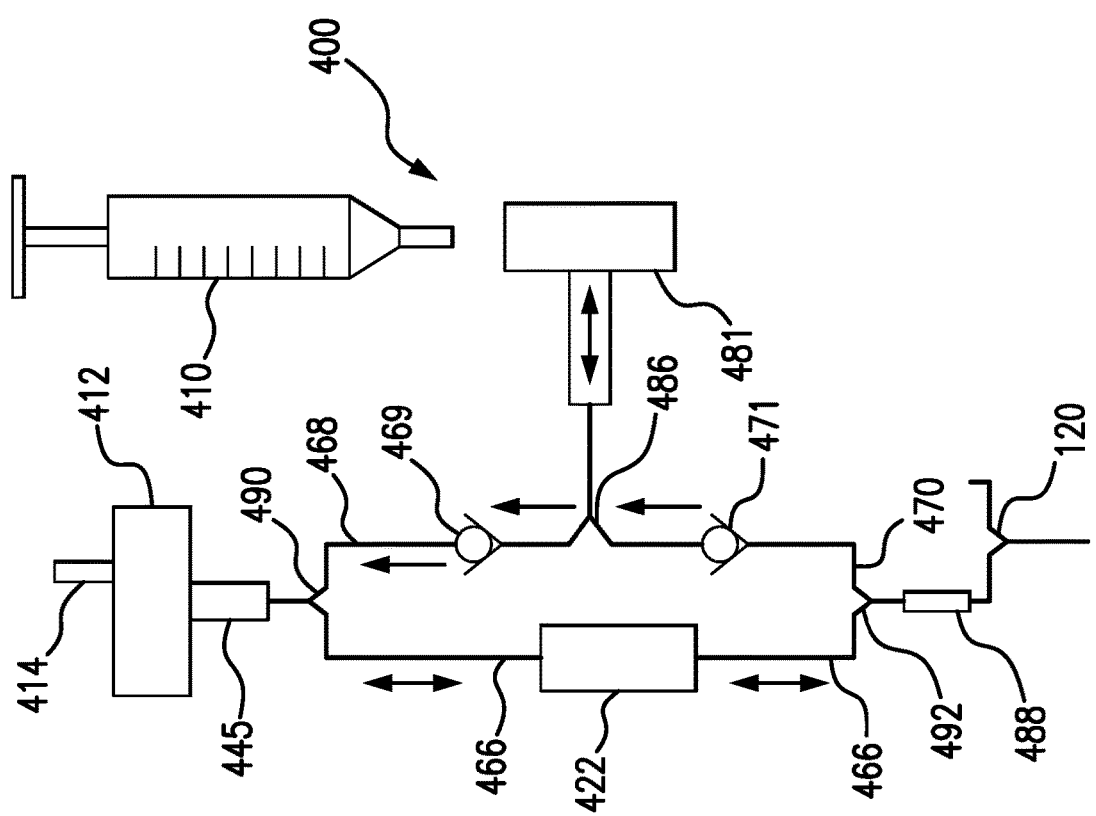
FIG. 4 illustrates an apparatus with which gastric residual volume ("GRV") evaluations may be implemented, according to an example embodiment of the present disclosure.

In some embodiments of an apparatus configured to perform gastric residual volume measurement, one or more of which are shown in FIG. 4, gastric residual volume measurement apparatus 400, for use with an enteral feeding system 100/200 and a collection reservoir 412, the function of which has been described above and is well known to those skilled in the art. Collection reservoir 412 has a vent 414 and a first relief tubing segment 445 that is connected to a second (intermediate) relief tubing segment 466 and a first bypass tubing segment 468. Likewise, a third relief tubing segment 488 is connected to the second (intermediate) relief tubing segment 466 and a second bypass tubing segment 470. The junction of the first relief tubing segment 445, the second relief tubing segment 466 and the first bypass tubing segment 468 can be any suitable 3-port device or its equivalent, for example a Y-connector 490. Similarly, the junction of the third relief tubing segment 488, the second relief tubing segment 466 and the second bypass tubing segment 470 can be any suitable 3-port device or its equivalent, for example a Y-connector 492. A clamping mechanism 422 is mounted to the second (intermediate) relief tubing segment 466 and can be any suitable clamp or other clamping means that permits selective closure of fluid flow through second (intermediate) relief tubing segment 466. The third relief tubing segment 488 can connect to a Y-connector 120, just as relief tubing 145 of FIG. 1 connects to Y-connector 120 in FIG. 1.

The first bypass tubing segment 468 and the second bypass tubing segment 470 are also connected to an access port 481, which can also be a suitable Y-connector 486 or comparable coupling device or structure. Port 481 in some embodiments is accessible by a fluid removal and reintroduction apparatus such as syringe 410 or other fluid withdrawal and pumping (i.e., "manmade force-applying") means capable of withdrawing reflux material from the second bypass tubing segment 470 and also capable of pumping reflux material into the first bypass tubing segment 468, as desired. The volumetric indicia on the syringe 410 may be used to measure the amount of reflux material collected from the patient. For example, a 50 mL syringe may be used to remove and measure reflux material by measuring the reflux material using the volumetric indicia. If the quantity of reflux material is more than the capacity of the syringe 410, the reflux material may be measured and placed into a container until it is reintroduced to the patient (e.g., four syringes of 50 mL and one syringe of 37 mL would indicate a gastric residual volume measurement of 237 mL). In another example embodiment, the fluid removal and reintroduction apparatus may include a syringe 410 and a measurement container that includes volumetric indicia. The syringe 410 may be used to remove reflux material via the access port 481 and place the removed reflux material into the measurement container. Then, the clinician may determine the gastric residual volume measurement using the volumetric indicia located on the measurement container.

First bypass tubing segment 468 has a first check valve 469 or other directionally limiting means that only permits fluid to flow (as indicated by the arrows) from the access port 481 to the collection reservoir 412 via first relief tubing segment 445. Similarly, second bypass tubing segment 470 has a second check valve 471 or other directionally limiting means that only permits fluid to flow (as indicated by the arrow) to the access port 481 from the patient via third relief tubing segment 488.

In operation, when active GRV measurement is to be performed using apparatus 400, clamping mechanism 422 is closed to prevent the movement of fluids (i.e., gases and/or liquids) through second (intermediate) relief tubing segment 466. A syringe 410 or other fluid withdrawal device (i.e., "manmade force-applying means") is connected to access port 481 (for example, using an ENFit connection configuration) and thereafter removes reflux material from apparatus 400 via second bypass tubing segment 470 and third relief tubing segment 488. If there is a substantial amount of reflux material and/or gastric contents to be removed (and perhaps measured), then multiple cycles of fluid withdrawal can be performed using port 481, or a larger fluid withdrawal device 410 can be used. Second check valve 471 permits fluid to flow from "below" second check valve 471 (i.e., any fluid below second check valve 471 in second bypass tubing segment 470, below clamping mechanism 422 in second (intermediate) relief tubing segment 466, in third relief tubing segment 488 and/or from any source connected to third relief tubing segment 488, including the patient's stomach). Withdrawal of fluid from apparatus 400 in this fashion does not affect or include any reflux material present "above" first check valve 469 (i.e., any fluid above first check valve 469 in first bypass tubing segment 468, above clamping mechanism 422 in second (intermediate) relief tubing segment 466, in first relief tubing segment 445 and/or in collection reservoir 412). If there is no fluid above first check valve 469, then the GRV of a patient can be measured accurately using the disclosed apparatus as described above.

The fluid path design configuration of first relief tubing segment 445, second relief tubing segment 466, first bypass tubing segment 468, second bypass tubing segment 470, and third relief tubing segment 488 and relative positioning of first check valve 469 and second check valve 470 can be designed to minimize or eliminate the potential for residual fluid remaining in first bypass segment 468 and second bypass tubing segment 470 following gastric content collection, GRV measurement, or gastric content return to the patient (if desired). Additionally, the system may be flushed of residuals using access port 481 and a syringe 410 filled with diluent or other suitable solution.

Similarly, if a GRV measurement has been made and some or all of the gastric contents are to be returned to the patient, then the syringe 410 or a suitable pumping mechanism (manmade force-applying means) can inject collected reflux material into apparatus 400 via access port 481. In this case, the injected fluids flow up through first check valve 469 into first relief tubing segment 445 and possibly the collection reservoir 412, but not through second bypass tubing segment 470, due to the directional orientation of second check valve 471. Once the desired amount of fluid has been injected into apparatus 400, clamping mechanism 422 can once again be opened to allow normal flow between collection reservoir 412 and a patient (e.g., for return of collected gastric contents).

In either method detailed above, a stopcock type connector or similar device may be used to select between channels (second relief tubing segment 466 or second bypass tubing segment 470) instead of using clamping mechanism 422. Such a connector could be made part of Y-connector 492 or used in place of Y-connector 492 with the dual purpose of providing a junction for third relief tubing segment 488, second relief tubing segment 466, and second bypass tubing segment 470 and selecting fluid flow in either a path through second relief tubing segment 466 or second bypass tubing segment 470.

In a slightly different methodology, the syringe 410 can be used in a cyclical or iterative fashion to withdraw fluid from apparatus 400, measure the fluid in the syringe 410, then immediately inject any withdrawn fluid back into apparatus 400. This iterative process permits expeditious measurement of gastric residual volume in an iterative process that does not require movement of the collection reservoir 412. Using this type of method, a syringe 410 having a 50 mL capacity could withdraw and inject 4 samples of fluid from apparatus 400, knowing that 200 mL had been measured and then deposited in collection reservoir 412 for later reintroduction to the patient's stomach. Alternatively, GRV can be measured by using volume graduation markings pre-established on the collection reservoir 412 via printing or the like.

Figure 5:
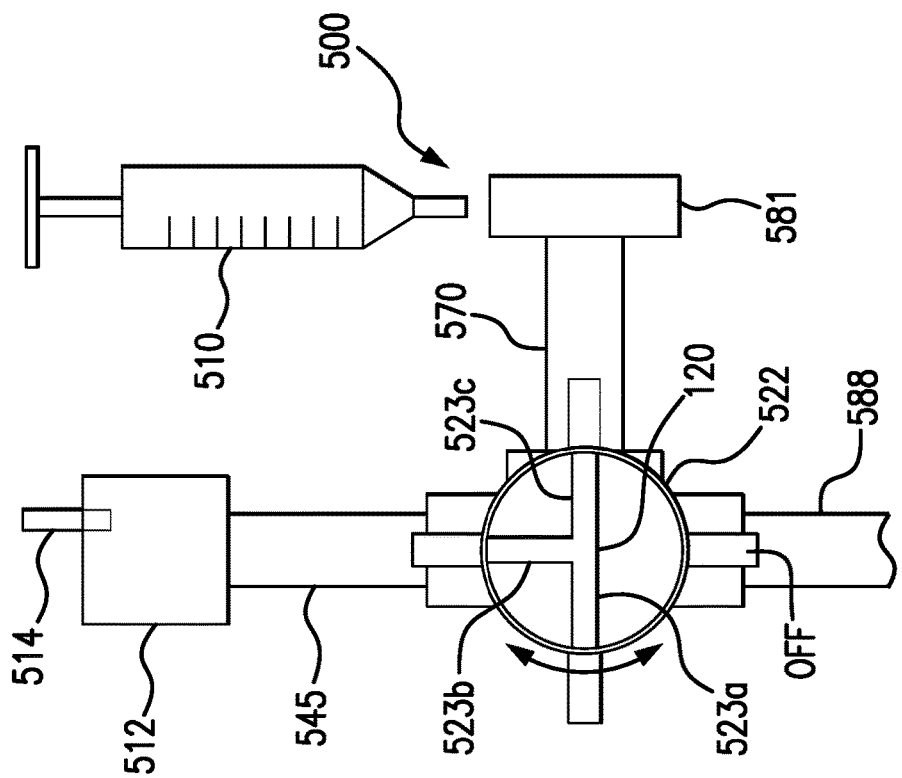
FIG. 5 illustrates apparatus with which GRV evaluations may be implemented, according to an example embodiment of the present disclosure.

The clamp and check valve configuration of FIG. 4 can be replaced by a three-way valve or stopcock, as seen in one or more embodiments in FIG. 5 that can be used in active GRV measurement. A gastric residual volume measurement apparatus 500, for use with an enteral feeding system 100/200 and a collection reservoir 512, the function of which has been described above and is well known to those skilled in the art. Collection reservoir 512 has a vent 514 and a first relief tubing segment 545 that is connected to a stopcock 522 or similar three-way valve. Stopcock 522 is also connected to a second relief tubing segment 588 and to a bypass tubing segment 570. The bypass tubing segment 570 is also connected to an access port 581, which can also be a suitable Y-connector or comparable coupling device or structure. Port 581 in some embodiments is accessible by a syringe 510 or other fluid withdrawal and injection means capable of withdrawing reflux material from the bypass tubing segment 570 and also capable of injecting reflux material into the bypass tubing segment 570, as desired.

Stopcock 522 is of standard construction and has sufficient inner diameters to accommodate any of the reflux material and/or other fluids that might be channeled between first relief tubing segment 545, second relief tubing segment 588 and bypass tubing segment 570. As is well know in the art, stopcock 522 is configured with a T-shaped fluid passageway 523 located in a plane of rotation that is the same as the plane as that defined by first relief tubing segment 545, second relief tubing segment 588 and bypass segment 570 as depicted in FIG. 5 (the three tubing segments do not have to be in the same plane in all embodiments, so long as the three-way valve used is able to provide suitable fluid communication between relevant tubing segments). Individual passages 523a, 523b, and 523c of the T-shaped fluid passageway 523 align and are placed in fluid communication with the various tubing segments to provide different fluid communication modes.

Stopcock 522 is capable of four flow positions. In a first position, bypass tubing segment 570 is shut off and first relief tubing segment 545 and second relief tubing segment 588 are in fluid communication. In a second position, first relief tubing segment 545 is shut off and bypass tubing segment 570 and second relief tubing segment 588 are in fluid communication. In a third position, as shown in FIG. 5, second relief tubing segment 588 is shut off and bypass tubing segment 570 and first relief tubing segment 545 are in fluid communication. Finally, in a fourth position, bypass tubing segment 570, first relief tubing segment 545 and second relief tubing segment 588 are all in fluid communication.

If GRV measurement is to be made, stopcock 522 is turned to the second position and the syringe 510 withdraws fluid from apparatus 500 via second relief tubing segment 588 and bypass tubing segment 570. This can be done as many times as necessary to accumulate all of the gastric contents required for GRV measurement. After measurement of the accumulated fluids, stopcock 522 can then be turned to the third position to permit injection of the collected fluids into reservoir 512 via bypass tubing segment 570 and first relief tubing segment 545. Once the desired amount of collected fluid has been placed in reservoir 512, stopcock 522 can then be turned to the first position to permit reintroduction of collected gastric contents to the patient's stomach using gravity to move the fluid from collection reservoir 512 to the patient via first relief tubing segment 545 and second relief tubing segment 588. The volumetric indicia on the syringe 510 may be used to measure the amount of reflux material collected from the patient. For example, a 50 mL syringe may be used to remove and measure reflux material by measuring the reflux material using the volumetric indicia. If the quantity of reflux material is more than the capacity of the syringe 510, the reflux material may be measured and placed into a container until it is reintroduced to the patient (e.g., four syringes of 50 mL and one syringe of 37 mL would indicate a gastric residual volume measurement of 237 mL). In another example embodiment, the fluid removal and reintroduction apparatus may include a syringe 510 and a measurement container that includes volumetric indicia. The syringe 510 may be used to remove reflux material via the access port 581 and place the removed reflux material into the measurement container. Then, the clinician may determine the gastric residual volume measurement using the volumetric indicia located on the measurement container.

As an additional option, the syringe 410/510 can be disengaged from the access port 481/581 following the collection of gastric aspirate. Once disconnected, a few drops of gastric aspirate from the syringe can be applied to pH paper or a pH meter to provide an extra check for feeding tube or sump tube placement. Per the NHS National Patient Safety Agency (NPSA) in the United Kingdom (UK), "pH between 1 and 5.5 as the safe range" for confirming the position of the feeding tube tip in the patient's stomach.

Collection Reservoir Material and Design

In earlier systems, collection reservoirs 112, 212, and 312 of FIGS. 1, 2A-2C, and 3A (hereinafter referred to as collection reservoir 112) have typically been a pliable bag made from a flexible elastomeric plastic such as polyethylene, ethylene-vinyl acetate (EVA), or polyvinylchloride (PVC). In some embodiments disclosed herein, collection reservoir 112 may instead be made of expandable or elastic material to allow for increasable capacity to retain reflux materials. Collection reservoir 112 can alternatively embody a more shape-retentive container such as a polyethylene or polypropylene plastic bottle, which can improve the ambulatory nature of gastric pressure relief system 110 and feeding systems 100/200, as well as providing other advantages. Such embodiments can use a rigid or semi-rigid reservoir to achieve such advantages. In some embodiments a hydrophobic material can be used so that liquid in the reservoir does not stick to walls or corners. Special bag material, or a bag material inner layer (in a multi-layer bag film material construction), or a coated material lining on the inside of the reservoir bag can be implemented to reduce surface tension. This enables more easily draining all liquid and reducing, minimizing and/or eliminating the liquid residuals upon draining gastric aspirate back to patient or discarding aspirate via a drain port. The collection reservoir 112 is closed to the entry of liquid and solid materials and does not allow pouring or introduction of formula or the like into the collection reservoir 112 and thus is easily distinguishable from the feeding container 146 of the system.

Figure 6A:
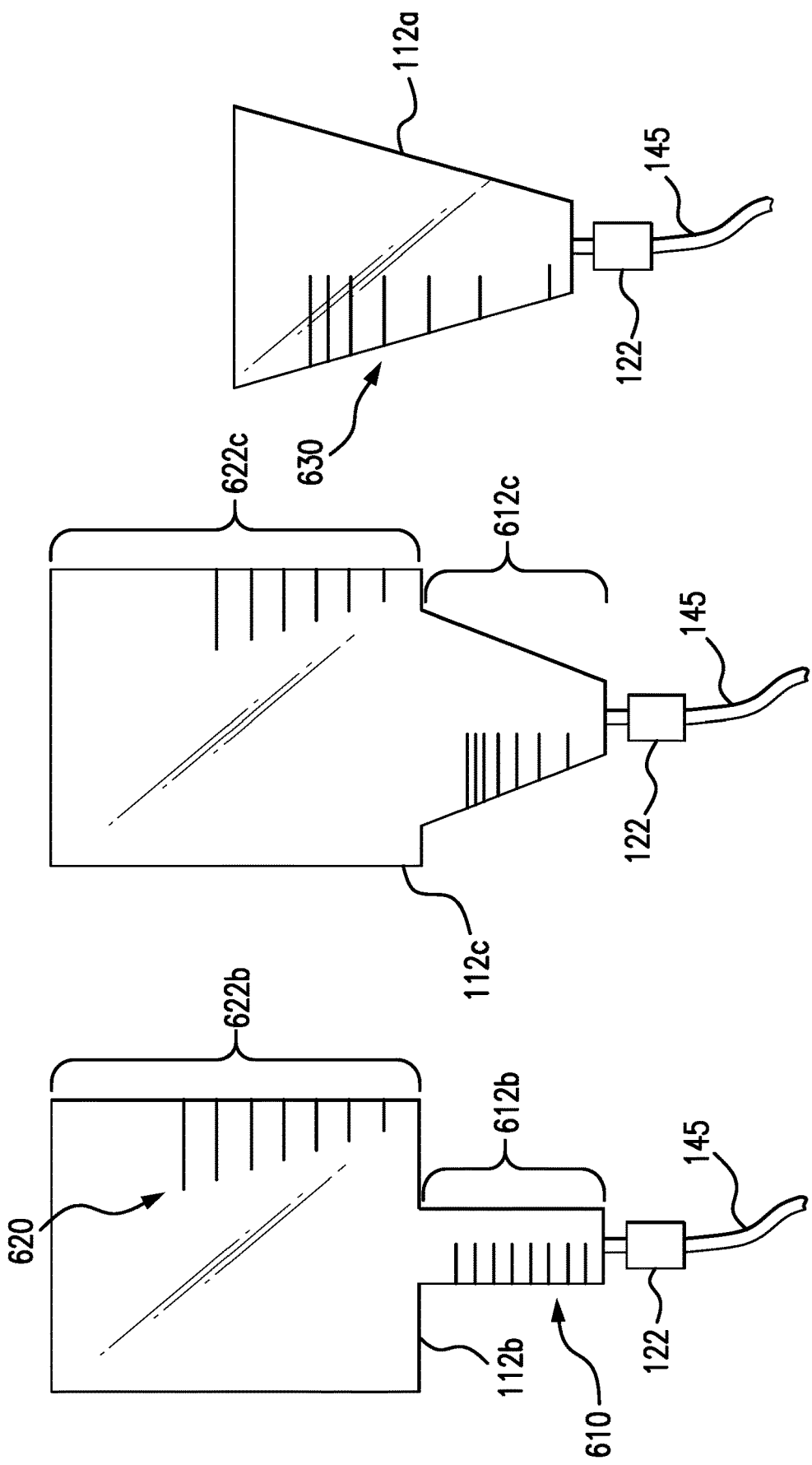
FIGS. 6A-6D illustrate various views of different embodiments of a reflux material collection reservoir that can be employed in connection with gastric pressure relief systems, according to an example embodiment of the present disclosure.
Figure 6B:
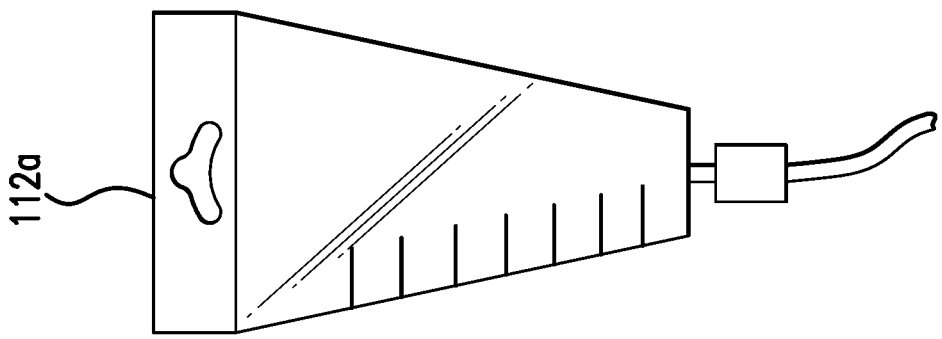
Figure 6B:
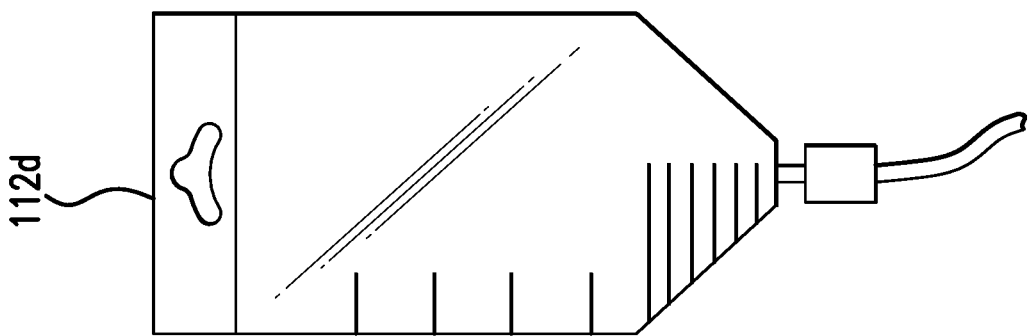
Figure 6B:
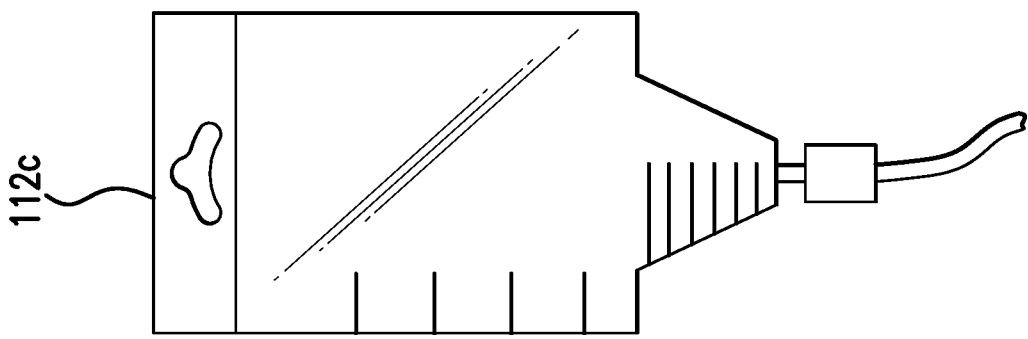
Figure 6B:
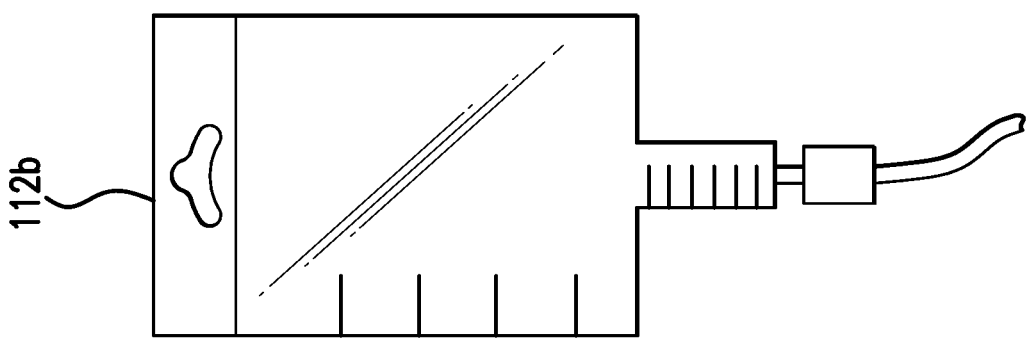

For example, if easy measurement viewing and improved monitoring are required or desired, a single-chambered, V-shaped or frusto-conical collection reservoir 112a as shown in FIG. 6A can be used with special markings and/or other indicia that make monitoring and tracking of fluid level easier (e.g., the collection reservoir 112a can have different colored levels and/or colored printing, as could the various tubing segments employed in such a system). Alternatively, stepped collection reservoir configurations 112b and 112c, also shown in FIG. 6A, can be employed in some embodiments, and use distinct sections in the reservoir to facilitate and/or improve measurement and monitoring of fluid levels, patient activity, etc. In an example embodiment, the volumetric indicia may be fine volumetric indicia 610, which include volume measurement indicia that are spaced closer together than other indicia on the collection reservoir 112. The fine volumetric indicia 610 provide more accurate volume readings in smaller volumetric increments of fluid (e.g., 5 mL and 10 mL). Additionally, the volumetric indicia may be course volumetric indicia 620, which include volume measurement indicia that are spaced further apart than other indicia on the collection reservoir 112. The course volumetric indicia 620 measure larger volume increments of fluid (e.g., 50 mL and 100 mL). In another example embodiment, the volumetric indicia may be variable volumetric indicia 630, which include volumetric indicia of variable spacing on the collection reservoir 112. The fine volumetric indicia 610 and the course volumetric indicia 620 may include indicia that are variably spaced or evenly spaced. Finally, as seen in FIG. 6B, a tapered collection reservoir configuration 112d can be used in which tapered narrowing of the reservoir's lower section provides easily read markings and/or other indicia of similar volume measurements. In many cases, the fluid accumulated from a patient does not fill the reservoir, so the stepped or other specialized configurations that have more precise and/or more easily readable indicators as shown with collection reservoirs 112a, 112b, 112c and 112d can be very helpful.

In each stepped collection reservoir configuration two chambers are identifiable and defined within the reservoir. The lower chamber 612 is connected to the relief tubing 145 and is configured to receive reflux materials from a patient with whom the gastric pressure relief system 110 is being used. Lower chamber 612b of reservoir 112b is cylindrical and holds a smaller volume to permit increased measuring accuracy (e.g., the lower chamber 612b may have a smaller diameter than its upper chamber 622b in some embodiments). The smaller volume in the lower chamber 612b permits more precise measurement and easier reading of liquid levels in reservoir 112b and thus assists a nurse or other caregiver in measuring changes to the reflux material level over time. The frusto-conical lower chamber 612c of reservoir 112c likewise provides such improved viewing and measurement monitoring. In similar fashion, the narrower diameter of the V-shaped or frusto-conical reservoir 112a and lower chamber of tapered configurations 112c and 112d permit such easier viewing and measurement monitoring for material initially collected in collection reservoir embodiments 112a, 112c and 112d though that ease of viewing is diminished as the diameter of the reservoir increases toward its upper end.

As the collection reservoir fills more, reading and measuring precision may become less important. In such cases, the lower chambers 612b, 612c of the stepped collection reservoir embodiments 112b, 112c, respectively, can be configured to hold an appropriate amount of fluid, for example on the order of 50 mL, 100 mL, 250 mL or 500 mL of fluid above (or taking into account) the connecting pressure relief tubing 145. Similarly, all or a part of the lower chamber and/or upper chamber of each collection reservoir embodiment 112b and 112c can be colored (or the measurement indicia color-coded), again to provide quick and reliable feedback to a nurse or other caregiver concerning the amount of refluxed material in the gastric pressure relief system 110. Color-coding can likewise be employed with collection reservoirs 112a and 112d. The volumetric measurement indicia on collection reservoirs 112a, 112b, 112c, 112d (generally referred to as collection reservoir 112) (which can be numerical and/or the use of colors or other non-numerical indicia) can be especially helpful when monitoring to detect one or more threshold levels of reflux materials, for example as indications of excessive internal stomach pressure within the patient's stomach, low digestion/acceptance rates of nutrient formula being supplied to the patient, etc.

Figure 6C:
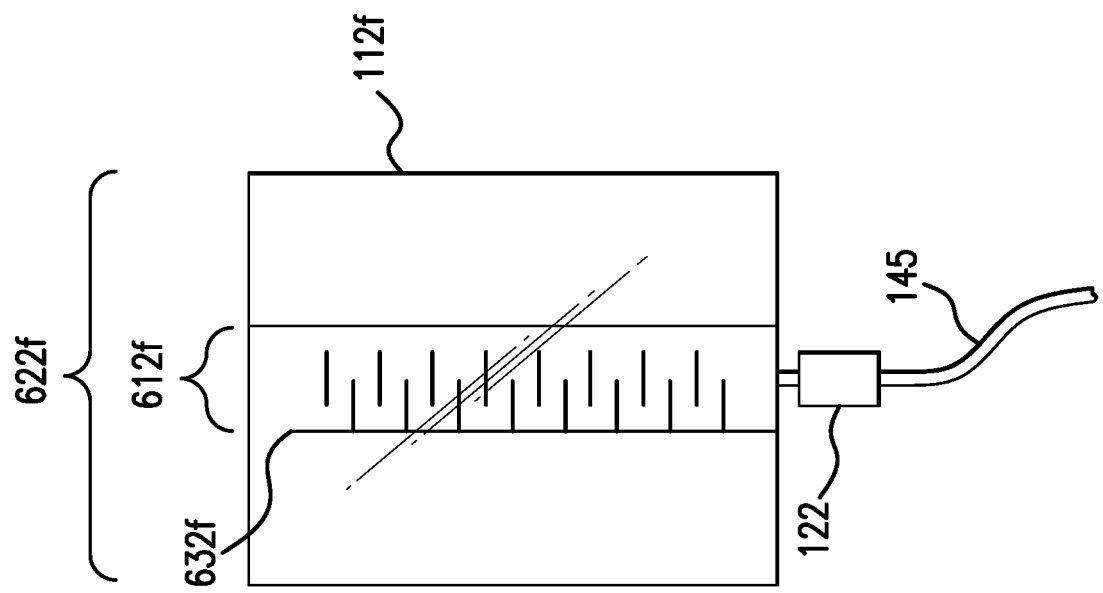
Figure 6C:
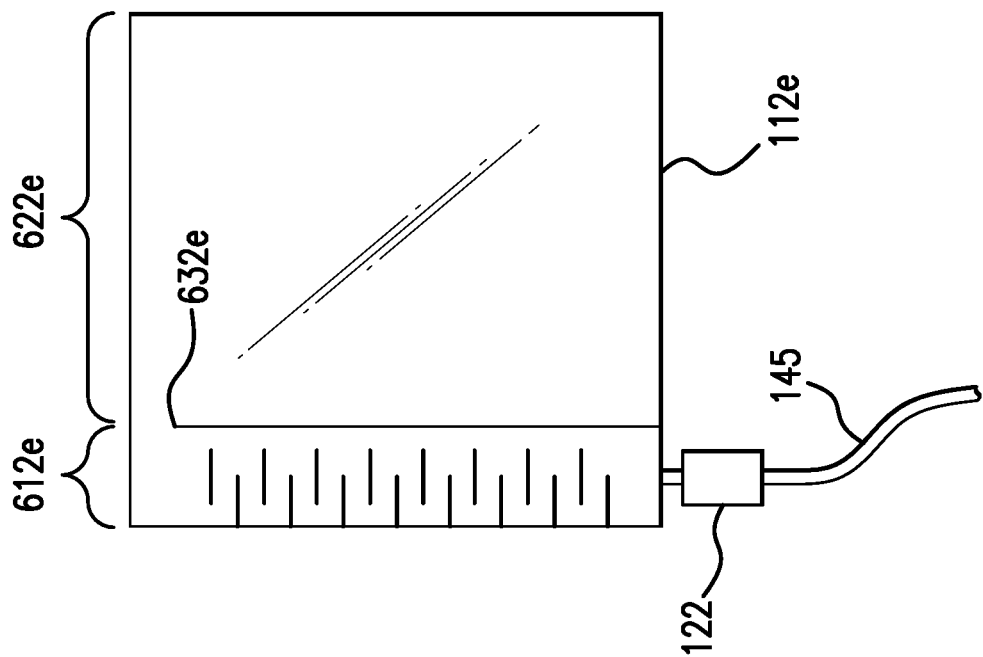
Figure 6D:
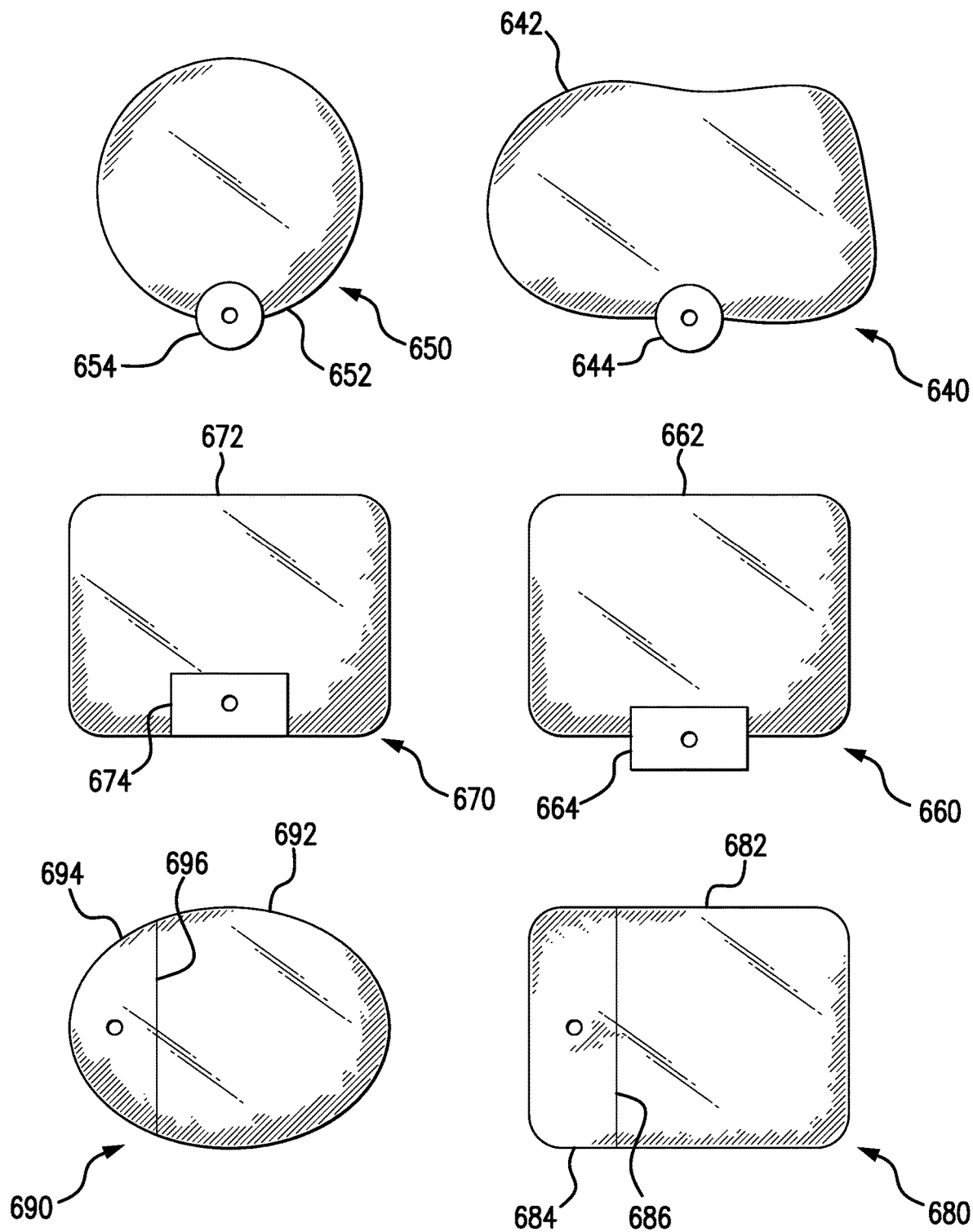

FIGS. 6C and 6D illustrate other embodiments of a collection reservoir that provide easy measurement and viewing, using laterally distinguished (i.e., side-by-side) chambers separated by a wall or the like rather than the vertically oriented chambers of collection reservoirs 112b and 112c, for example. In these lateral-chamber embodiments the first chamber is side-by-side with the second chamber and the two chambers can be at approximately the same vertical level. FIG. 6C provides side views of one or more embodiments of a collection reservoir that includes a first chamber that provides easier viewing and measurement of initial reflux materials. In reservoir 112e, a first chamber 612e (e.g., a side chamber) is connected to relief tubing 145 so that any reflux materials that flow back to collection reservoir 112e initially collect in the first chamber 612e (e.g., the side chamber), which has easily readable markings. Once first chamber 612e (e.g., side chamber) has filled to capacity, an overflow wall 632e permits reflux material overflow to fill the second chamber 622e (632e and 632f can be generally referred to as wall 632). This configuration permits the collection reservoir to maintain a smaller configuration while providing easily read measurement of reflux materials. Likewise, collection reservoir 112f has a similar small-diameter first chamber 612f that permits easy reading and overflow via wall 632f into second chamber 622f as needed (622e and 622f can be generally referred to as second chamber 622).

FIG. 6D illustrates top views of one or more of collection reservoirs 112e, 112f, depending on several variable characteristics of each collection reservoir configuration. In the collection reservoir 640 of FIG. 6D (which can be a top view of reservoir 112e and/or 112f of FIG. 6C), the second chamber 642 is a pliable or flexible bag that is coupled to a rigid first chamber 644. This permits compact and easy storage of collection reservoirs 640 during manufacturing and prior to use with the advantages of a dual-chamber configuration. The first chamber 644 can have whatever cross-section is best suited for its intended manufacture, packaging and use. Similarly, in collection reservoir 650 of FIG. 6D (which also can be a top view of collection reservoir 112e and/or 112f of FIG. 6C), the first chamber (e.g., side chamber) again is a rigid tube 654 or the like, but second (larger) chamber 652 also is rigid in this configuration, thus providing a shape-retentive construction that might be preferable in some circumstances. In similar fashion, collection reservoir 660 of FIG. 6D (which again can be a top view of collection reservoir 112e and/or 112f of FIG. 6C), uses square or rectangular cross-sectioned chambers 662, 664, as does the collection reservoir 670 of FIG. 6D, which has chambers 672, 674. Again, equally spaced increments or measurement indicators are used on first chamber configurations that have consistent diameter spacing; tapered diameter spacing in the first chamber requires appropriately spaced indicators.

Other embodiments of the collection reservoir include reservoir 680 of FIG. 6D, which can be a top view of collection reservoir 112e of FIG. 6C, has a unitary rigid rectangular structure that is divided by wall 686 into first chamber 684 and second chamber 682. Finally, collection reservoir 690 of FIG. 6D, which also can be a top view of collection reservoir 112e of FIG. 6C, has a unitary rigid ovate or circular structure that is divided by wall 696 into first chamber 694 and second chamber 692.

Thus, as can be seen from the examples noted above, first and second chambers of a given collection reservoir configuration can be constructed of the same or different materials and a variety of cross-sectional shapes to provide desired manufacturing, packaging and performance characteristics. In similar fashion, with respect to the vertically distinguished chambers of collection reservoir 112b and collection reservoir 112c, the lower chamber of a stepped configuration can be rigid while the upper chamber (e.g., chamber 622b or 622c) or other section or portion of the collection reservoir is pliable plastic, elastomeric material, etc.

The collection reservoir must have adequate capacity to receive a substantial amount of reflux material in the event of excessive gastric pressure. For example, when gastric pressure relief system 110 of FIG. 1 is utilized in enteral feeding of adults, collection reservoir 112 preferably has a fluid capacity of approximately 500 mL. Collection reservoir 112 is scaled smaller for small patients (e.g. pediatric and neonatal patients) based on their smaller size and commensurately smaller gastric capacity. Historically, flexible/pliable plastic bags for medical fluid use have been standardized on 50 mL, 100 mL, 250 mL, 500 mL, and 1 L sizes. Guidelines have been published by the American Society for Parenteral and Enteral Nutrition (ASPEN), including a 2009 guideline publication that recommends not to hold enteral nutrition (EN) for gastric residual volumes <500 mL in the absence of other signs of intolerance. See, "Guidelines for the provision and assessment of nutrition support therapy in the adult critically ill patient: Society of Critical Care Medicine and American Society for Parenteral and Enteral Nutrition: Executive Summary" (Crit Care Med 2009 Vol. 37, No. 5). Smaller bag sizes (e.g. 250 mL or 100 mL) can be used for neonates who require less gastric volume.

Figure 7A:
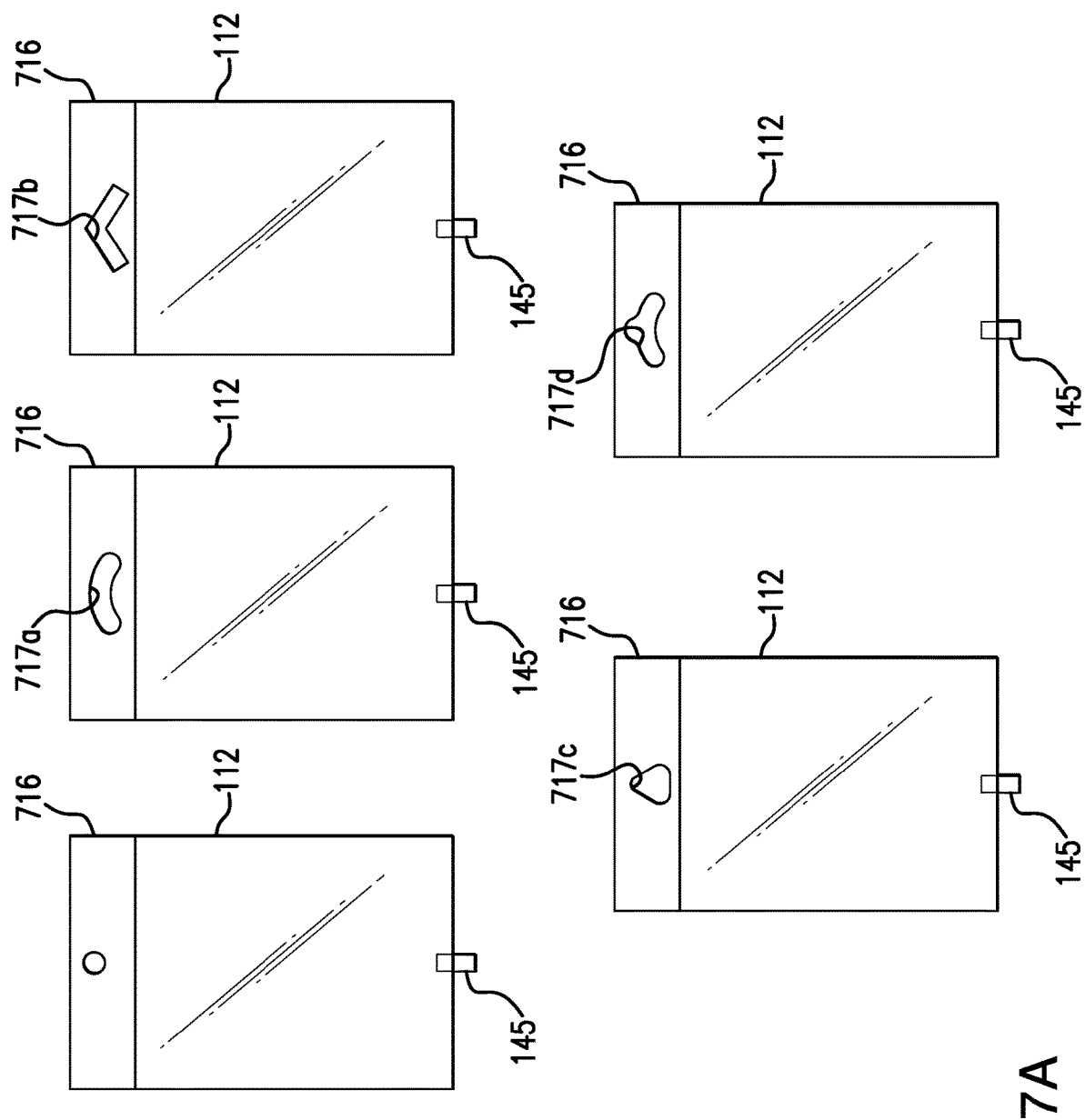
FIGS. 7A and 7B illustrate various views of different embodiments of hanger tabs for a reflux material collection reservoir that can be employed in connection with gastric pressure relief systems, according to an example embodiment of the present disclosure.
Figure 7B:
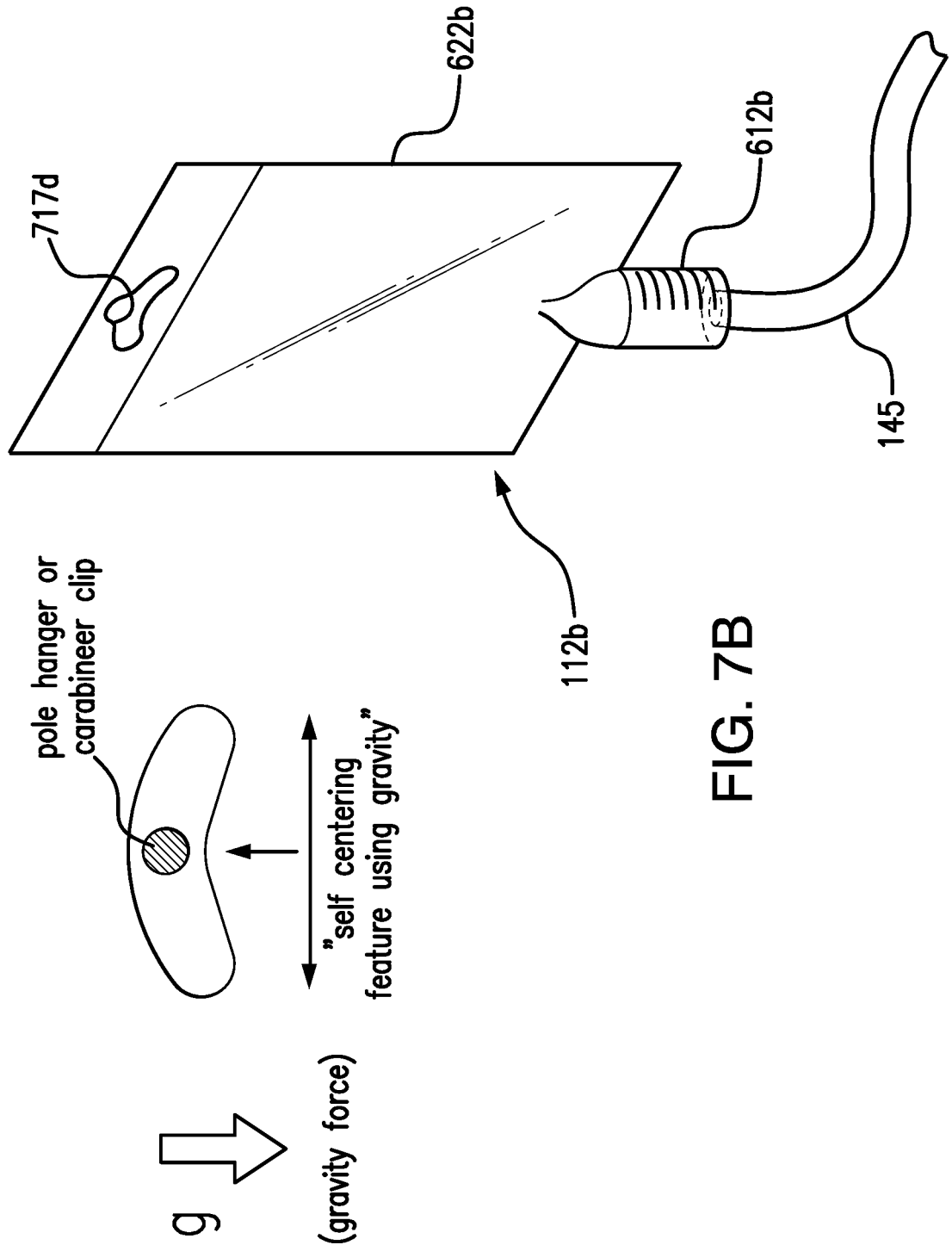

In settings where the collection reservoir 112 is susceptible to movement while suspended from a support stand 130 or the like, a self-centering hanger feature for collection reservoir 112 can be implemented, as seen in several exemplary embodiments in FIG. 7A. As illustrated in FIG. 7B, the force of gravity (g) acts on the various hanger aperture embodiments as shown. In one example a crescent-shaped aperture 717a in hanger tab 716 is used. In another illustrated example an inverted V-shaped aperture 717b is used instead. A rounded triangular aperture 717c provides a hanger tab with a less elongated hole, where the vertices of the triangle shape have been rounded. Finally, a notched crescent aperture 717d can be implemented as well. In each of these examples, the aperture 717 provides a self-centering feature based on gravity. One example of collection reservoir 112b of FIG. 6A is shown in FIG. 7B, wherein collection reservoir 112b has a lower first chamber 612b that is a rigid, reduced diameter measurement chamber and further wherein the second, upper chamber 622b is pliable plastic or the like that can be suspended using a notched crescent aperture 717d. In addition, mechanisms that make collection reservoir 112 easily transferable (e.g., carabiner clips and the like) can be employed to have a simple, portable and easily attached/detached apparatus for hanging in various locations. Accordingly, the enteral feeding system 100/gastric pressure relief system 110 is provided with a collection reservoir hanging apparatus to advantageously suspend the collection reservoir 112 in centered position from the support stand 130.

Vent Shape & Material

In earlier systems, vent 114 has been a tube or other hollow, solid element that allowed gas to escape collection reservoir 112 to the atmosphere. The "open" nature of such earlier vents 114 has limited the use and versatility of reservoirs using such vents. Moreover, if vent 114 is an opening to the interior of collection reservoir 112, then a closed liquid system is not maintained in system 100.

Figure 8A:
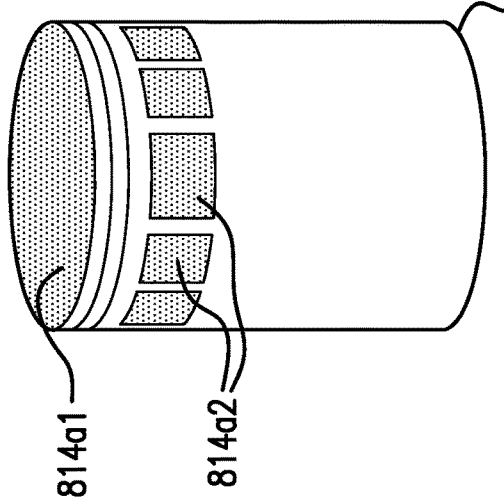
FIGS. 8A-8F illustrate various example embodiments of membrane-implemented vents for an enteral feeding and gastric decompression system collection reservoir, according to an example embodiment of the present disclosure.
Figure 8B:
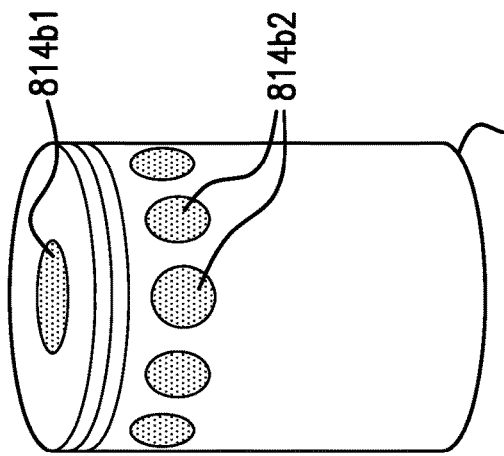
Figure 8C:
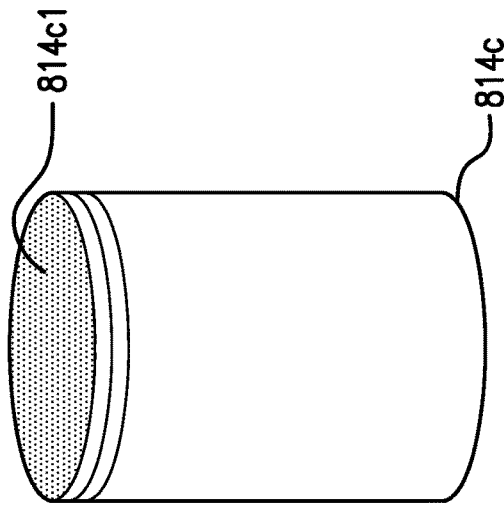
Figure 8D:
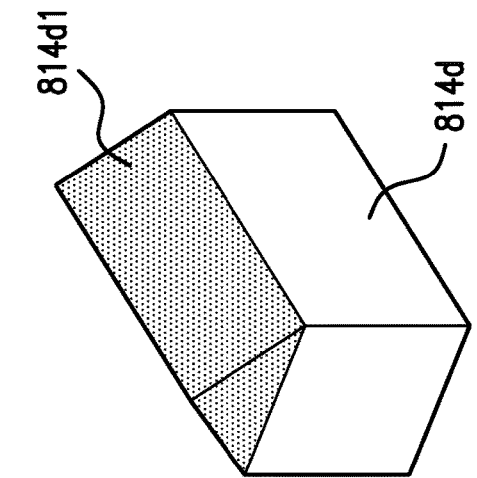
Figure 8E:
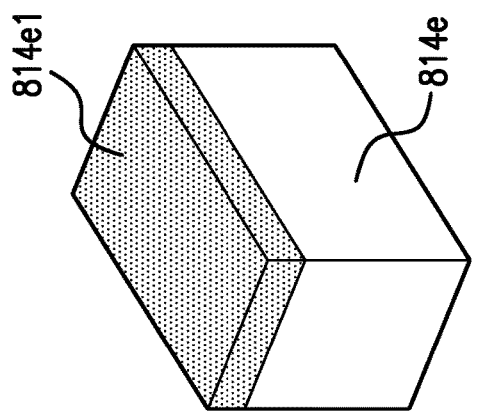
Figure 8F:
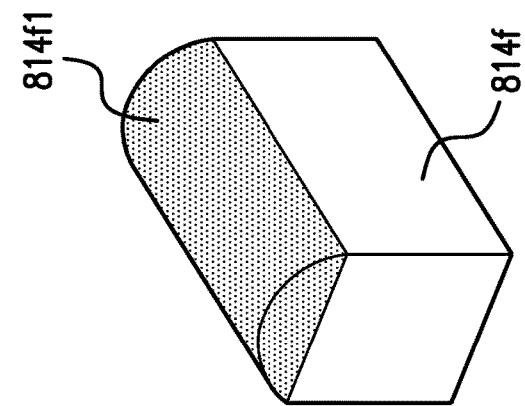

Embodiments of the present disclosure permit escape of gases from a collection reservoir using vents that comprise one or more membranes, some embodiments of which are shown in FIGS. 8A through 8F. Vent 814a of FIG. 8A illustrates a vent having a top membrane 814a1 as well as side rectangular membranes 814a2. Likewise, vent 814b of FIG. 8B has top and side membranes, though of different shapes and/or sizes, such as top membrane 814b1 and side elliptical membranes 814b2. In yet a different embodiment, vent 814c of FIG. 8C shows a top membrane 814c1 affixed to an otherwise standard vent tube. Finally, a vent shaft of rectangular cross-section has a "rooftop" configured membrane 814d1 as part of vent 814d in FIG. 8D. Other configurations similar to vent 814d could be rectangular or "roof-shaped" (e.g., as seen as membrane 814e1 of vent 814e illustrated in FIG. 8E), semicircular (e.g., as seen as membrane 814f1 of vent 814f illustrated in FIG. 8F), etc. in relation to the cross section of the vent area section (vent 814a, 814b, 814c, 814d,814e, and 814f can be generally referred to as vent 814).

In embodiments where one or more membranes are used, each such membrane can be selected from an appropriate range of materials and configurations (e.g., a hydrophobic and/or oleophobic membrane made of materials such as those produced by Gore and Trinity Technology Group (TTG), for example a membrane material can be an acrylic copolymer membrane cast on a nonwoven nylon support. It can be treated for desired performance regarding oleophobicity and/or hydrophobicity).

For example, the breathability (i.e., measure of air permeability—typically measured by the Gurley number), liquid surface tension (force exerted by below-the-surface molecules upon those at the surface-air interface), solids surface-free energy (force exerted by below-the-surface molecules upon those at the surface-air interface), the membrane's wet-out properties (filling membrane pores with fluid), etc. can be important factors for membrane selection.

Where the collection reservoir is used in settings where collection reservoir contents are likely to come into frequent contact with the vent, vent embodiments are used that resist "wetting" that reduces its efficiency. The membrane also can be of a suitable shape, surface area and location to provide desired operational characteristics. For example, as shown in FIGS. 8A through 8F, vents 814a, 814b, 814d, 814e, and 814f (and perhaps other embodiments) make complete covering of each vent unlikely when it is used in a backpack or other setting in which the collection reservoir might shift and/or when other materials might come into contact with the vent while the enteral feeding system and associated gastric pressure relief system 110 is in use.

Drain Port & Bag Disconnect

It is desirable to maintain an enteral feeding system as a "closed system" to prevent accidental contamination of system, contents, and eventually the patient. Additionally, a "closed system" protects the clinician, caregiver, and/or patient from exposure to the gastric bodily fluid, nutrients, and medications inherent in any enteral delivery system. Embodiments disclosed herein implement an "on demand only" drain port, quick disconnect feature, and/or other access apparatus in such a system, as discussed in more detail below (e.g., for the collection reservoir, feeding container and/or relief segment).

Figure 9A:
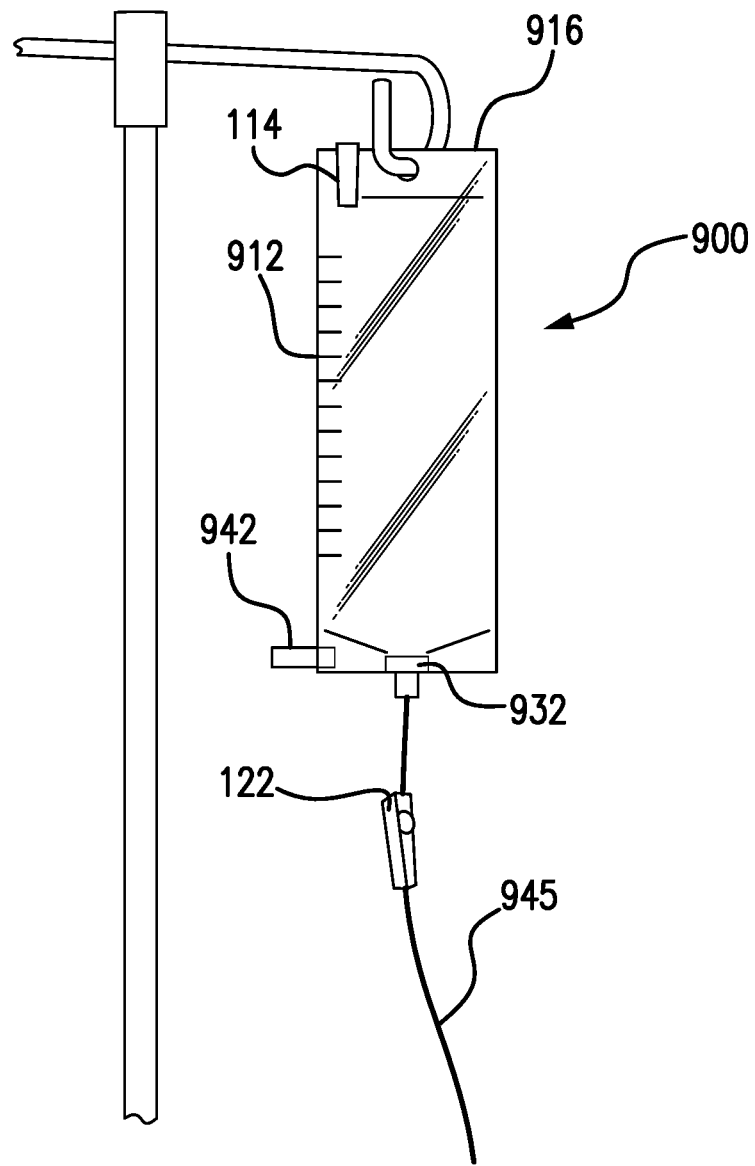
FIG. 9A illustrates an example embodiment of a quick-release connector and a drain for an enteral feeding and gastric decompression system collection reservoir, according to an example embodiment of the present disclosure.
Figure 9B:
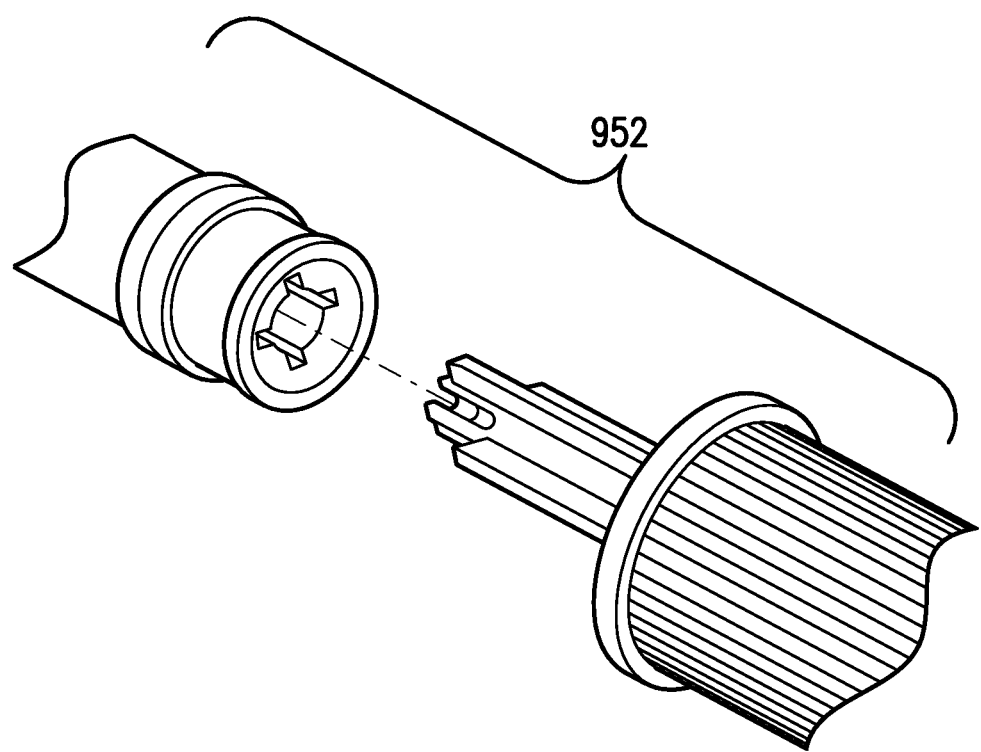
FIG. 9B illustrates an example embodiment of a quick-release connector, according to an example embodiment of the present disclosure.

A quick-release connector apparatus 932, as seen in FIG. 9A, can be provided at the connection between collection reservoir 912 and relief tubing 945 in enteral feeding system 900 to facilitate changing of collection reservoirs and/or as an alternative means for draining collection reservoir 912, for example as part of GRV procedures or the like as defined and discussed herein and with respect to earlier technologies. Connector apparatus 932 can include or be in addition to a drain port 942 that can be used to remove collected contents, for example via the GRV collection process, or to facilitate using system 900 in an initial gastric contents draining function, as in the "raising of the reservoir" example discussed in more detail below. If a drain port 942 is implemented, it must seal effectively (e.g., using a screw connector, an ENPlus enteral feeding connection system (one example of which is shown as connector 952 in FIG. 9B), or a similar sealing connector design appropriate for enteral and/or gastric decompression/relief applications).

In addition to facilitating connection and disconnection of the relief tubing 945 to and from the collection reservoir 912, quick-release connector apparatus 932 can also be replicated in an upper end of an enteral feeding container that is part of system 900 to facilitate transfer of the contents of collection reservoir 912 to enteral feeding container using mating quick-release connector ports or other similar apparatus. In some embodiments such transfers can be made while the collection reservoir 912 and enteral feeding container are both in use, or one or both can be disconnected from operation and the transfer performed in that disconnected state.

A rigid reservoir can improve the ambulatory nature of an enteral feeding system as well. In such embodiments, the reservoir can include drain port 942 to permit easy removal and discarding of residuals and the like, as seen in FIG. 9A. To facilitate changing of reservoirs (or an alternative to drain the reservoir) a quick-release connector apparatus 932 as seen in FIG. 9A can be provided at reservoir's connection to any associated tubing. Moreover, easily transferable mechanisms (e.g., carabiner clips and the like) can be employed to have a simple, portable and easily attached/detached apparatus. In addition, connector apparatus 932 can include a drain to permit easy removal, sampling, or discarding of gastric residuals.

Placement Reminder

Figure 10:
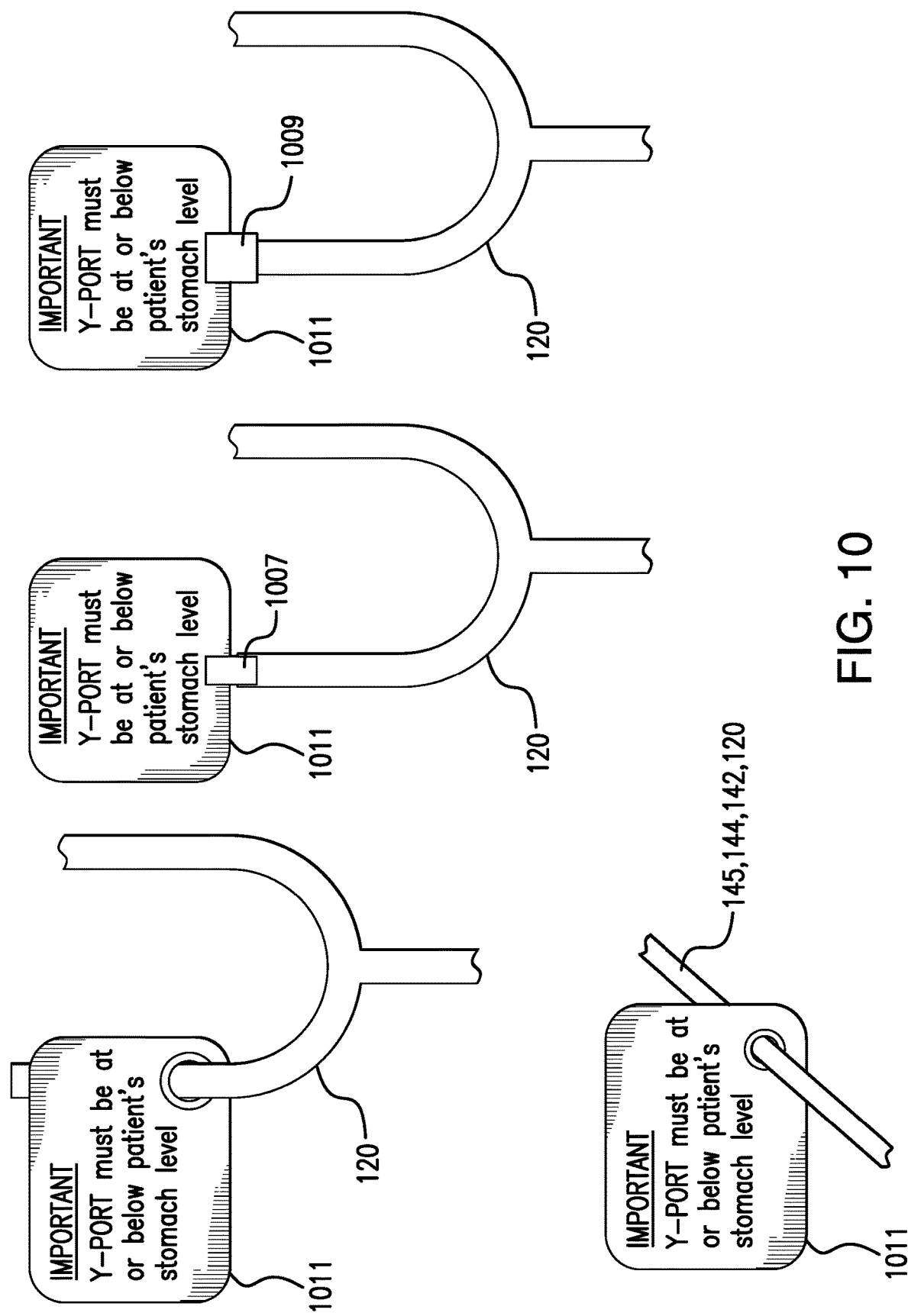
FIG. 10 illustrates exemplary embodiments of placement reminders, according to an example embodiment of the present disclosure.

In some embodiments, for example as shown in FIG. 10, a placement reminder 1011 (e.g., in the form of a reminder tab, label, tag, flag, or the like) that can be attached to the Y-connector 120 prior to one or more of the relief tubing 145, the administration tubing 142 and/or the fluid delivery tubing 144 being inserted into connector 120. This placement reminder 1011 can take the form of a tag, label or tape affixed to Y-connector 120 or other system component in a manner that compels a user to consider the placement reminder 1011 and check the level of Y-connector 120 relative to the patient's stomach level before commencing use of gastric pressure relief system 110. The placement reminder 1011 can have a hole that allows it to on to Y-connector 120 or one of the tubing segments. Similar informational messaging can also be printed, embossed, etc. on one of the tubing segments such as administration tubing 142, fluid delivery tubing 144, relief tubing 145 and/or elsewhere on one or more components of the apparatus. In other embodiments shown in FIG. 10, a plug 1007 to which placement reminder 1011 is attached can be inserted into at least one open arm of Y-connector 120, thus requiring a nurse or other user to remove plug 1007, thus preventing connection of Y-connector 120 to a tubing segment unless plug 1007 is removed first. Plug 1007 also can be in the shape of a chip or tab that has printed on it a reminder that Y-connector 120 must be at or below the patient's stomach before using the gastric pressure relief system 110. Another alternative is a cap 1009 to which placement reminder 1011 is attached that can be affixed to or over one or more arms of Y-connector 120, again requiring removal of the placement reminder 1011 prior to use of Y-connector 120. Placement reminder 1011 thus reduces the chances that a nurse or other user forgets to place and maintain Y-connector 120 at or below the patient's stomach level. The label itself can be made of paper, materials made from flashspun high-density polyethylene fibers, materials made from nonwoven spunbound olefin fibers, plastic, or any other suitable material and can be brightly colored to further enhance its advisory effect. Accordingly, the enteral feeding system 100/gastric pressure relief system 110 is provided with a placement reminder apparatus to advantageously inform the clinician about the proper usage level of the Y-connector 120 relative to the level of a patient's stomach.

Flow Indicia

Figure 11:
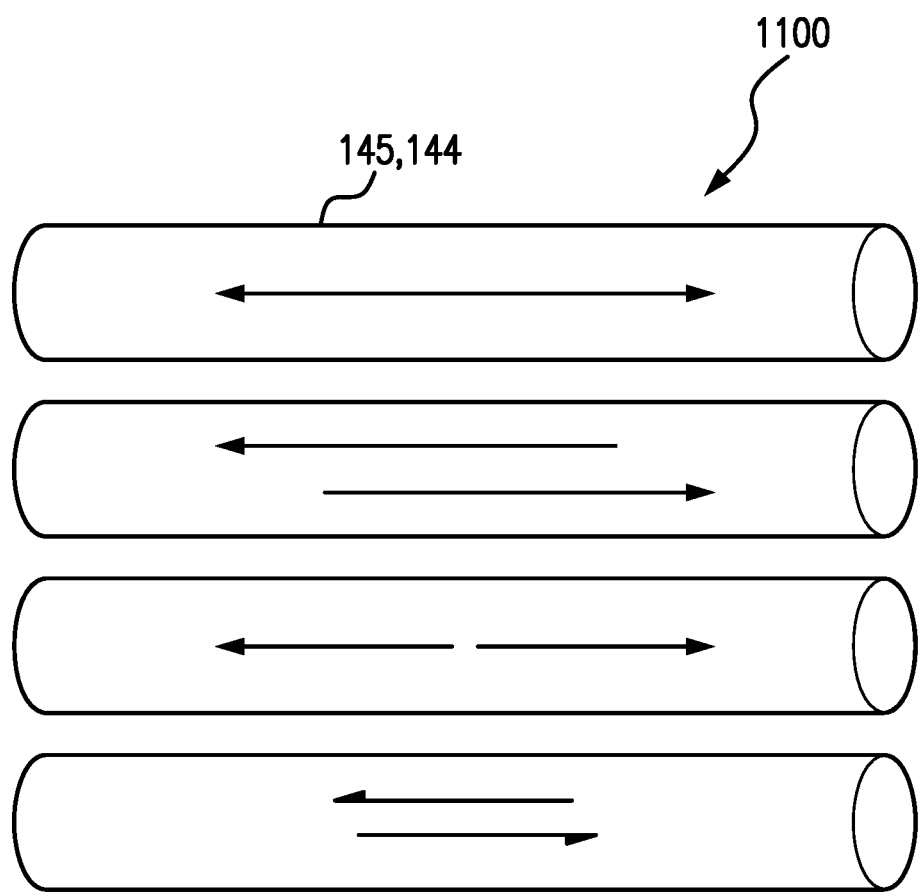
FIG. 11 illustrates several exemplary embodiments of bidirectional flow indicia and/or markings on tubing segments, according to an example embodiment of the present disclosure.

To assist in viewing and tracking reflux material levels, some embodiments of the gastric pressure relief system 110 include one or more tubing segments on which bidirectional flow indicia 1100 are printed, embossed or otherwise viewable. Such bidirectional flow indicia 1100 can include arrows or the like, exemplary embodiments of which are seen in FIG. 11. When such bidirectional flow indicia 1100 are provided in a repeating or other patterned way, an individual can track, recognize, etc. movement of the fluid level within such a tubing segment. In some embodiments, such bidirectional flow indicia 1100 can be used in connection with colored segments of tubing or other highlights to facilitate reading and recognition of changing fluid levels within the tubing. In the gastric pressure relief system 110 and the enteral feeding system 100 of FIG. 1, for example, relief tubing segment 145 and fluid delivery tubing segment 144 could both have such bidirectional flow indicia 1100 (in some cases, in addition to volumetric indicia or the like).

In embodiments using a multi-chamber reservoir 112 or other reservoir embodiment, threshold marking(s) may be provided to alert a nurse or caregiver to specific formula/reflux volume levels. For example, a given marking on reservoir 112 (including a colored indicator, for example) might alert one to the likelihood of an occlusion in the feeding system, or to the presence of feeding intolerance (e.g., vomiting, retching, excess fluid from impaired gastric motility), delayed gastric emptying or gastrointestinal obstruction.

Graduated Raising of the Reservoir

One or more method embodiments involving enteral feeding are shown in FIGS. 12A-12D. Nutrient flow is prevented using a clamping mechanism 1222 or the like with administration tubing segment 1242, which is connected to Y-connector 1220. A reservoir 1212 has an initial position near the lowest level of common intravenous suspension stand 1290. After the gastric contents of the patient have been collected in collection reservoir 1212 via feeding tube 1288, Y-connector 1220 and relief tubing 1245, the enteral feeding nutrient flow from feeding container 1246 is initiated and gradual raising of collection reservoir 1212 thereafter commences. In such methods, shown in FIGS. 12A-12D, use of the enteral feeding system 1200 begins with the collection reservoir 1212 suspended at a location well below its nominal operational position, for example near the floor 1295 and below the level of a patient 1285. The collection reservoir 1212 is raised in a stepwise progression (for example, by 1 foot or other selected increments) to provide initial draining of the patient's gastric contents when collection reservoir 1212 is raised from a starting position shown in FIG. 12A to a first intermediate position shown in FIG. 12B. Additional draining of the patient's gastric contents occurs when the collection reservoir 1212 is raised from the first intermediate position shown in 12B to a second intermediate position shown in FIG. 12C. Similarly, additional draining of the patient's gastric contents occurs when the collection reservoir 1212 is raised from the second intermediate position shown in FIG. 12C to a nominal position shown in FIG. 12D. Gradual reintroduction of some or all of those initially collected gastric contents occurs as the collection reservoir is raised in a step-wise progression from a starting position to a nominal position as feeding progresses. GRV evaluation might be conducted prior to initiating nutrient flow from feeding container 1246 via administration tubing 1242.

Full, normal nutrient flow and gastric reflux material equilibrium is achieved with each step until the collection reservoir 1212 is at its nominal position, shown in FIG. 12D. Equilibrium can be recognized by viewing the stability of the fluid level in relief tubing 1245 that indicates that the apparatus 1200 is ready to provide nutrients to a patient. The fluid level is determined to be stable (i.e., not changing), for example, if the fluid level remains the same over a period of time (e.g., a minute). For example, the clinician may view the fluid level and then re-check the stability of the fluid level after a period of time (e.g., a minute) to determine that equilibrium has been reached (i.e., the fluid is at substantially the same level after re-checking). First, the clinician positions the collection reservoir 1212 in the starting position, shown in FIG. 12A to allow gastric material to flow from the patient's stomach and drain into the collection reservoir 1212. Then, the clinician may want to reintroduce the collected gastric material back into the patient's stomach. To do this, the clinician may raise the collection reservoir 1212 from the starting position to a first intermediate position to provide initial draining of gastric material from the collection reservoir 1212 back to the patient's stomach (i.e., from FIG. 12A to 12B). Once it is determined that gastric reflux material equilibrium is achieved at the first intermediate position, the clinician may raise the collection reservoir 1212 from the first intermediate position to the second intermediate position (i.e., from FIG. 12B to 12C). Then, after determining that gastric reflux material equilibrium is achieved at the second intermediate position, the clinician may raise the collection reservoir 1212 from the second intermediate position to the nominal position (i.e., from FIG. 12C to 12D). In an example embodiment, a different number of intermediate positions may be used in the stepwise progression of raising the collection reservoir 1212 (e.g., four or six intermediate positions). This process might be accomplished using a pulley-type apparatus 1275 above collection reservoir 1212 in some embodiments. In other embodiments collection reservoir 1212 can be suspended with a cord 1292 or other line that has linking points that can be progressively linked to stand 1290 as the collection reservoir 1212 is raised. As can be appreciated from the foregoing description, collection reservoir 1212 can be raised and feeding rate increased as the patient begins to tolerate enteral feeding (i.e., digestion) until the collection reservoir 1212 is raised until the patient can tolerate the operation of enteral feeding system 1200 with collection reservoir 1212 hung in its standard position at or above the feeding container or other feeding source.

This methodology is a good alternative when the patient's condition and situation would call for it, the advantages being that a clinician can take pressure off the gastric surgery area initially and gradually ease the patient back to full enteral feeding as they can tolerate it based again on their particular clinical state.

Aspects of the subject matter described herein may be useful alone or in combination with any one or more of the other aspect described herein. Without limiting the foregoing description, in an exemplary aspect of the present disclosure, a gastric pressure relief system includes a feeding container connected to administration tubing, relief tubing, a delivery tube in fluid communication with the administration tubing and the relief tubing, a multi-way connector, a collection reservoir, and a flow regulator. The multi-way connector has a first arm, a second arm, and a third arm. Additionally, the first arm is connected to the relief tubing, the second arm is connected to the delivery tube, and the third arm is connected to the administration tubing. The collection reservoir is in fluid communication with the relief tubing. Additionally, the collection reservoir includes a vent configured to allow gas to pass through in both directions, the collection reservoir is configured to collect reflux fluids from a patient's stomach via the relief tubing, and the collection reservoir comprises volumetric indicia configured to represent a volume of reflux fluids received from the patient's stomach. The flow regulator adapted to regulate flow within the relief tubing.

In accordance with another exemplary aspect of the present disclosure, which may be used in combination with the preceding aspect, the multi-way connector is a Y-connector.

In accordance with another exemplary aspect of present disclosure, which may be used in combination with the preceding aspects, the flow regulator is configured to selectively an adjustable limit the flow of fluid through the relief tubing.

In accordance with another exemplary aspect of the present disclosure, which may be used in combination with any one or more of the preceding aspects, the flow regulator is either manually controlled or automatically controlled.

In accordance with another exemplary aspect of the present disclosure, which may be used in combination with any one or more of the preceding aspects, the flow regulator is a roller clamp.

In accordance with another exemplary aspect of the present disclosure, which may be used in combination with any one or more of the preceding aspects, the gastric pressure relief system further includes a detector coupled to the collection reservoir. The detector is configured to detect one or more characteristics of the collection reservoir. The flow regulator is coupled to the detector for controlling the flow of fluids between the multi-way connector and the collection reservoir, and the flow regulator is configured to selectively and adjustably limit the flow of fluid through the relief tubing.

In accordance with another exemplary aspect of the present disclosure, which may be used in combination with any one or more of the preceding aspects, the detector includes either a hanging weight scale or a weight load cell. The flow regulator further includes a digital controller in communication with the detector. The flow regulator includes an adjustable clamp configured to apply pressure to the relief tubing, and the amount of pressure applied to the relief tubing is based on measurement data from the detector.

In accordance with another exemplary aspect of the present disclosure, which may be used in combination with any one or more of the preceding aspects, a location apparatus configured to be used with a gastric pressure relief system, the location apparatus being interposed between a feeding container and a delivery tube, the location apparatus having administration tubing connected to the feeding container, the location apparatus includes relief tubing, a multi-way connector, a collection reservoir, and a clip. The relief tubing is in fluid communication with the administration tubing and the delivery tube. The multi-way connector has a first arm, a second arm, and a third arm. The first arm is connected to the relief tubing, the second arm is connected to the delivery tube, and the third arm is connected to the administration tubing. The collection reservoir in fluid communication with the relief tubing. Additionally, the collection reservoir includes a vent configured to allow gas to pass through in both directions, the collection reservoir is configured to collect reflux fluids from a patient's stomach via the relief tubing, and the collection reservoir comprises volumetric indicia configured to represent a volume of reflux fluids received from the patient's stomach. The clip is configured to maintain the multi-way connector in a position at or below a patient's stomach level.

In accordance with another exemplary aspect of the present disclosure, which may be used in combination with any one or more of the preceding aspects, the location apparatus further includes a weight affixed to the multi-way connector configured to assist in maintaining the placement of the multi-way connector at or below the level of the patient's stomach.

In accordance with another exemplary aspect of the present disclosure, which may be used in combination with any one or more of the preceding aspects, the multi-way connector is constructed of a first material having a sufficient weight to assist in maintaining the placement of the multi-way connector at or below the level of the patient's stomach.

In accordance with another exemplary aspect of the present disclosure, which may be used in combination with any one or more of the preceding aspects, the clip is a clothing clip.

In accordance with another exemplary aspect of the present disclosure, which may be used in combination with any one or more of the preceding aspects, the multi-way connector is a Y-connector.

In accordance with another exemplary aspect of the present disclosure, which may be used in combination with any one or more of the preceding aspects, a gastric pressure relief system includes a feeding container, relief tubing, a delivery tube, a multi-way connector, a collection reservoir, and a check valve. The feeding container is connected to administration tubing. The delivery tube is in fluid communication with the administration tubing and the relief tubing. The multi-way connector has a first arm, a second arm, and a third arm. Additionally, the first arm is connected to the relief tubing, the second arm is connected to the delivery tube, and the third arm is connected to the administration tubing. The collection reservoir is in fluid communication with the relief tubing. The collection reservoir includes a vent configured to allow gas to pass through in both directions, and the collection reservoir is configured to collect reflux fluids from a patient's stomach via the relief tubing. The check valve is configured to permit flow in one direction from the administration tubing to either the relief tubing or the delivery tube.

In accordance with another exemplary aspect of the present disclosure, which may be used in combination with any one or more of the preceding aspects, the check valve is an internal valve positioned within the third arm of the multi-way connector.

In accordance with another exemplary aspect of the present disclosure, which may be used in combination with any one or more of the preceding aspects, the check valve is interposed between the multi-way connector and administration tubing.

In accordance with another exemplary aspect of the present disclosure, which may be used in combination with any one or more of the preceding aspects, the collection reservoir includes volumetric indicia configured to represent a volume of reflux fluids received from the patient's stomach.

In accordance with another exemplary aspect of the present disclosure, which may be used in combination with any one or more of the preceding aspects, a gastric pressure relief system includes a feeding container, relief tubing, a delivery tube, a multi-way connector, a collection reservoir, and a gastric residual volume measurement apparatus. The feeding container is connected to administration tubing. The delivery tube is in fluid communication with the administration tubing and the relief tubing. The multi-way connector has a first arm, a second arm, and a third arm. Additionally, the first arm is connected to the relief tubing, the second arm is connected to the delivery tube, and the third arm is connected to the administration tubing. The collection reservoir is in fluid communication with the relief tubing. The collection reservoir includes a vent configured to allow gas to pass through in both directions, and the collection reservoir is configured to collect reflux fluids from a patient's stomach via the relief tubing. The gastric residual volume measurement apparatus is interconnected to the relief tubing between the collection reservoir and the multi-way connector.

In accordance with another exemplary aspect of the present disclosure, which may be used in combination with any one or more of the preceding aspects, the gastric residual volume measurement apparatus includes a first relief tubing segment in fluid communication with a second relief tubing segment and a first bypass tubing segment, a first multi-way connector, a third relief tubing segment in fluid communication with the second relief tubing segment and a second bypass tubing segment, a second multi-way connector, a regulator, an access port, a first check valve, and a second check valve. The first bypass tubing segment has a first end and a second end. The first relief tubing segment has a first end and a second end connected to the reservoir, and the second relief tubing segment has a first end and a second end. The first multi-way connector has a first arm, a second arm, and a third arm. The first end of the second relief tubing segment is connected to the first arm. The first end first bypass tubing segment is connected to the second arm, and the first end of the first relief tubing segment is connected to the third arm. The third relief tubing segment has a first end connected to the first arm of the multi-way connector and a second end, and the second bypass tubing segment has a first end and a second end. The second multi-way connector has a third arm, a fourth arm, and a fifth arm. The second end of the second relief tubing segment is connected to the fourth arm. The second end of the second bypass tubing segment is connected to the fifth arm, and the second end of the third relief tubing segment is connected to the sixth arm. The regulator is connected to the second relief tubing segment adapted to control flow through the second relief tubing segment. The access port is in fluid communication with the first bypass tubing segment and the second bypass tubing segment. The access port has a first port, a second port, and a third port. The second end of the first bypass tubing segment is connected to the first port, the first end of the second bypass tubing segment is connected to the second port, and the third port is configured for removal of reflux material by a fluid removal and reintroduction apparatus having volumetric indicia. The first check valve is positioned within the first bypass tubing segment adapted to directionally limit fluid flow from the access port to the reservoir. The second check valve is positioned within the second bypass tubing segment adapted to directionally limit fluid flow from the third relief tubing segment to the access port.

In accordance with another exemplary aspect of the present disclosure, which may be used in combination with any one or more of the preceding aspects, the gastric residual volume measurement apparatus includes a first relief tubing segment, a second relief tubing segment, a bypass tubing segment, a multi-way valve, and an access port. The first relief tubing segment has a first end connected to the reservoir and a second end. The bypass tubing segment has a first port, a second port, and a third port. The second end of the first relief tubing segment is connected to the first port of the multi-way valve. The second relief tubing segment is connected to the second port of the multi-way valve, and the second end of the bypass tubing segment is connected to the third port of the multi-way valve. The multi-way valve is configured to selectively permit fluid flow through at least two tubing segments at any given time. The access port has a first port and a second port. The first end of the bypass tubing segment is connected to the first port of the access port, and the second port is configured for removal of reflux material by a fluid removal and reintroduction apparatus having volumetric indicia.

In accordance with another exemplary aspect of the present disclosure, which may be used in combination with any one or more of the preceding aspects, a placement reminder apparatus is configured to be used with a gastric pressure relief system, the placement reminder apparatus is also configured to be interposed between the distal end of a delivery tube and a feeding container connected to administration tubing, the placement reminder apparatus includes a multi-way connector, relief tubing, a collection reservoir, and a placement reminder. The multi-way connector is configured to connect the administration tubing to the delivery tube. The relief tubing is connected to the multi-way connector. The collection reservoir is connected to the relief tubing. Additionally, the collection reservoir is configured to collect reflux fluids from a patient's stomach via the relief tubing. The placement reminder is configured to be affixed to the gastric pressure relief system and includes information about the proper usage level of the connector relative to the level of a patient's stomach when the gastric pressure relief system is in use.

In accordance with another exemplary aspect of the present disclosure, which may be used in combination with any one or more of the preceding aspects, the delivery tube includes fluid delivery tubing and a feeding tube. The fluid delivery tubing is connected to the feeding tube by a tube connector, and the fluid delivery tubing is connected to the multi-way connector.

In accordance with another exemplary aspect of the present disclosure, which may be used in combination with any one or more of the preceding aspects, the placement reminder is connected to the multi-way connector.

In accordance with another exemplary aspect of the present disclosure, which may be used in combination with any one or more of the preceding aspects, the placement reminder includes a plug inserted into an arm on the multi-way connector, a cap covering an arm on the multi-way connector, and/or a tag affixed to the multi-way connector.

In accordance with another exemplary aspect of the present disclosure, which may be used in combination with any one or more of the preceding aspects, the tag is affixed to the multi-way connector using at least one of: (i) adhesive, (ii) tape, and (iii) a clip.

In accordance with another exemplary aspect of the present disclosure, which may be used in combination with any one or more of the preceding aspects, an apparatus for relieving gastric pressure during enteral feeding, the apparatus is interposed between an enteral feeding tube and an administration tubing segment connected to a fluid nutrient source, the apparatus includes a fluid delivery tube, a connector, relief tubing, a collection reservoir; and bidirectional flow markings. The fluid delivery tubing is connected to the feeding tube. The connector is configured to connect the administration tubing to the fluid delivery tubing. The relief tubing is connected to the connector. Additionally, the collection reservoir is connected to the relief tubing. The collection reservoir is configured to collect reflux fluids from a patient's stomach via the relief tubing. The bidirectional fluid flow markings are included on at least one of the sections of tubing include the relief tubing, the administration tubing, and the delivery tube. The bidirectional markings are used to inform users of the gastric pressure relief system of the bidirectional flow of fluids within any tubing segment marked with the bidirectional fluid flow markings.

In accordance with another exemplary aspect of the present disclosure, which may be used in combination with any one or more of the preceding aspects, a method of reintroducing gastric material to a patient includes restricting flow of nutrients from a feeding container, initiating gradual raising of a collection reservoir from a starting position to a nominal position, wherein the starting position is below a patient's stomach level, and raising the collection reservoir in a stepwise progression to provide initial draining when the collection reservoir is in a first intermediate position, wherein raising the collection reservoir to the next stepwise progression is not performed until gastric reflux material equilibrium is achieved.

In accordance with another exemplary aspect of the present disclosure, which may be used in combination with any one or more of the preceding aspects, a collection reservoir raising apparatus includes a support stand, a collection reservoir, a delivery tube, and a connector. The collection reservoir is in fluid communication with relief tubing. Additionally, the collection reservoir includes a vent configured to allow gas to pass through in both directions, and the collection reservoir is configured to collect reflux fluids from a patient's stomach via the relief tubing. The connector is in fluid communication with the relief tubing and the delivery tube. The pulley is connected to the support stand, and the cord connected to the collection reservoir, wherein the cord is configured to fit through the pulley and raise the collection reservoir.

In accordance with another exemplary aspect of the present disclosure, which may be used in combination with any one or more of the preceding aspects, a collection reservoir can be used in connection with an enteral feeding system that includes relief tubing, a connector, and a delivery tube. The collection reservoir includes at least two chambers configured to receive gastric reflux materials from an enteral feeding system relief tubing.

In accordance with another exemplary aspect of the present disclosure, which may be used in combination with any one or more of the preceding aspects, the at least two chambers include a first chamber and a second chamber. The first chamber is configured to receive gastric reflux materials from relief tubing of an enteral feeding system. The second chamber configured to receive gastric reflux materials from the first chamber. The first chamber includes volumetric indicia configured to represent a volume of reflux material received from the enteral feeding system, the second chamber is configured to receive gastric reflux materials only after the first chamber is completely filled, and at least one of said first and second chambers includes a vent configured to permit gas to exit the collection reservoir.

In accordance with another exemplary aspect of the present disclosure, which may be used in combination with any one or more of the preceding aspects, the second chamber is provided without volumetric indicia.

In accordance with another exemplary aspect of the present disclosure, which may be used in combination with any one or more of the preceding aspects, the first chamber and the second chamber are laterally situated and are separated by an internal overflow wall.

In accordance with another exemplary aspect of the present disclosure, which may be used in combination with any one or more of the preceding aspects, the first chamber includes a rigid material and the second chamber includes either a rigid material or a pliable material.

In accordance with another exemplary aspect of the present disclosure, which may be used in combination with any one or more of the preceding aspects, the at least two chambers include a first chamber and a second chamber. The first chamber is configured to receive gastric reflux materials from relief tubing of an enteral feeding system. The second chamber is configured to receive gastric reflux materials from the first chamber. The second chamber is positioned above the first chamber, the second chamber is in fluid communication with the first chamber, the first chamber has a top end having a first width and a bottom end having a second width, and the second chamber has a bottom end having a third width.

In accordance with another exemplary aspect of the present disclosure, which may be used in combination with any one or more of the preceding aspects, the width of the first chamber is smaller than the third width of the second chamber.

In accordance with another exemplary aspect of the present disclosure, which may be used in combination with any one or more of the preceding aspects, the first width of the first chamber is smaller than the third width of the second chamber, and the second width of the second chamber is smaller than the first width of the first chamber.

In accordance with another exemplary aspect of the present disclosure, which may be used in combination with any one or more of the preceding aspects, the first chamber includes a first plurality of volume measurement indicia, the second chamber includes a second plurality of volume measurement indicia, and the first plurality of volume measurement indicia include smaller volume increments than the second plurality of volume measurement indicia.

In accordance with another exemplary aspect of the present disclosure, which may be used in combination with any one or more of the preceding aspects, a collection reservoir for use in connection with an enteral feeding system including relief tubing, a connector, and a delivery tube, the collection reservoir includes a frusto-conical chamber configured to receive gastric reflux materials from enteral feeding system gastric pressure relief tubing. The frusto-conical chamber is defined by a wall comprised of either a rigid material or a pliable material. The wall further includes volumetric indicia configured to represent a volume of reflux material received from the enteral feeding system.

In accordance with another exemplary aspect of the present disclosure, which may be used in combination with any one or more of the preceding aspects, collection reservoir hanging apparatus for use with a gastric pressure relief system includes a feeding container, relief tubing, a delivery tube, a multi-way connector, and a collection reservoir. The feeding container is connected to administration tubing. The delivery tube is in fluid communication with the administration tubing and the relief tubing. The multi-way connector has a first arm, a second arm, and a third arm. Additionally, the first arm is connected to the relief tubing, the second arm is connected to the delivery tube, and the third arm is connected to the administration tubing. The collection reservoir is in fluid communication with the relief tubing. The collection reservoir includes a vent configured to allow gas to pass through in both directions. The collection reservoir is configured to collect reflux fluids from a patient's stomach via the relief tubing. The collection reservoir includes a hanger tab with a self-centering aperture, and the collection reservoir includes volumetric indicia configured to represent a volume of reflux fluids received from the patient's stomach.

In accordance with another exemplary aspect of the present disclosure, which may be used in combination with any one or more of the preceding aspects, the self-centering aperture includes one of the following shapes: (i) a crescent, (ii) an inverted V-shape; (iii) a notched crescent; and (iv) a triangle having rounded vertices.

In accordance with another exemplary aspect of the present disclosure, which may be used in combination with any one or more of the preceding aspects, a gastric pressure relief system includes a feeding container connected to administration tubing, relief tubing, a delivery tube, a multi-way connector, a collection reservoir, and a drain port. The delivery tube is in fluid communication with the administration tubing and the relief tubing. The multi-way connector having a first arm, a second arm, and a third arm. Additionally, the first arm is connected to the relief tubing, the second arm is connected to the delivery tube, and the third arm is connected to the administration tubing. The collection reservoir is in fluid communication with the relief tubing. Additionally, the collection reservoir includes a vent configured to allow gas to pass through in both directions, the collection reservoir is configured to collect reflux fluids from a patient's stomach via the relief tubing, and the collection reservoir includes volumetric indicia configured to represent a volume of reflux fluids received from the patient's stomach. The drain port connected to the collection reservoir.

In accordance with another exemplary aspect of the present disclosure, which may be used in combination with any one or more of the preceding aspects, the drain port includes a quick-release connector.

In accordance with another exemplary aspect of the present disclosure, which may be used in combination with any one or more of the preceding aspects, an apparatus for relieving gastric pressure during enteral feeding, the apparatus is interposed between a feeding tube and administration tubing connected to a feeding container. The apparatus includes a multi-way connector, a fluid delivery tube, relief tubing, and a collection reservoir. The fluid delivery tubing is connected to the feeding tube. The multi-way connector is configured to connect the administration tubing to the fluid delivery tubing. The fluid delivery tubing has a first length defined by the minimum length required to position the multi-way connector at a patient stomach level when the feeding tube is providing fluid nutrient to a patient. The relief tubing is connected to the multi-way connector. The collection reservoir is connected to the relief tubing, and the collection reservoir is configured to collect reflux fluids from a patient's stomach via the relief tubing.

In accordance with another exemplary aspect of the present disclosure, which may be used in combination with any one or more of the preceding aspects, the multi-way connector is a Y-connector.

In accordance with another exemplary aspect of the present disclosure, which may be used in combination with any one or more of the preceding aspects, a method for providing gastric pressure relief during enteral feeding, wherein the enteral feeding is implemented using a feeding container that delivers fluid nutrient to a feeding tube via administration tubing, and a gastric pressure relief system is interposed between the administration tubing and the feeding tube. The method includes intubating the feeding tube in a patient, measuring the approximate shortest distance between the feeding tube proximal end and a vertical plane at the level of the patient's stomach, setting the length of the fluid delivery tubing segment to approximately the measured shortest distance, coupling the fluid delivery tubing to the feeding tube and to a multi-way connector, and providing fluid nutrient to the patient. The feeding tube has a proximal end outside the patient's body.

In accordance with another exemplary aspect of the present disclosure, which may be used in combination with any one or more of the preceding aspects, the measuring the approximate shortest distance is achieved by estimating the distance.

In accordance with another exemplary aspect of the present disclosure, which may be used in combination with any one or more of the preceding aspects, a gastric pressure relief system includes a feeding container, relief tubing, a delivery tube, a multi-way connector, and a collection reservoir. The feeding container is connected to administration tubing. The delivery tube is in fluid communication with the administration tubing and the relief tubing. The multi-way connector has a first arm, a second arm, and a third arm. Additionally, the first arm is connected to the relief tubing, the second arm is connected to the delivery tube, and the third arm is connected to the administration tubing. The collection reservoir in fluid communication with the relief tubing. Additionally, the collection reservoir includes a vent that is configured to allow gas to pass through in both directions. The vent includes one or more membranes configured to restrict the flow of liquid through the vent, and the collection reservoir is configured to collect reflux fluids from a patient's stomach via the relief tubing.

In accordance with another exemplary aspect of the present disclosure, which may be used in combination with any one or more of the preceding aspects, the one or more membranes includes at least one first membrane and at least one second membrane. The vent includes a top surface and a side surface, the at least one first membrane is included on the top surface of the vent, and the at least one second membrane is included on the side surface on the vent.

In accordance with another exemplary aspect of the present disclosure, which may be used in combination with any one or more of the preceding aspects, the one or more membranes are located on a side surface of the vent.

In accordance with another exemplary aspect of the present disclosure, which may be used in combination with any one or more of the preceding aspects, the one or more membranes are located on a top surface of the vent.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. An enteral feeding gastric pressure relief system comprising:
    a feeding container connected to an administration tubing;
    a relief tubing;
    a delivery tube in fluid communication with the administration tubing and the relief tubing;
    a multi-way connector having a first arm, a second arm, and a third arm, wherein
        the first arm is connected to the relief tubing,
        the second arm is connected to the delivery tube, and
        the third arm is connected to the administration tubing;
    a collection reservoir in fluid communication with the relief tubing, wherein the collection reservoir includes a vent configured to allow gas to pass through in both directions and at least one chamber configured to collect reflux fluids from a patient's stomach via the relief tubing;
    a gastric residual volume measurement apparatus interconnected to the relief tubing between the collection reservoir and the multi-way connector; and
    a check valve configured to permit flow in one direction from the administration tubing to either the relief tubing or the delivery tube.

2. The enteral feeding gastric pressure relief system of claim 1, wherein the check valve is an internal valve positioned within the third arm of the multi-way connector.

3. The enteral feeding gastric pressure relief system of claim 1, wherein the check valve is interposed between the multi-way connector and the administration tubing.

4. The enteral feeding gastric pressure relief system of claim 1, wherein the collection reservoir comprises volumetric indicia configured to represent a volume of reflux fluids received from the patient's stomach.

5. The enteral feeding gastric pressure relief system of claim 1, wherein the mufti-way connector is a Y-connector.

6. The enteral feeding gastric pressure relief system of claim 1, further comprising a flow regulator adapted to regulate flow within the relief tubing.

7. The enteral feeding gastric pressure relief system of claim 6, further comprising a detector coupled to the collection reservoir and configured to detect one or more characteristics of the collection reservoir, wherein
    the flow regulator is coupled to the detector for controlling the flow of fluids between the multi-way connector and the collection reservoir, and
    the flow regulator is configured to selectively and adjustably limit the flow of fluid through the relief tubing.

8. The enteral feeding gastric pressure relief system of claim 7, wherein the detector comprises either a hanging weight scale or a weight load cell, and further wherein the flow regulator further comprises a digital controller in communication with the detector, the flow regulator comprises an adjustable clamp configured to apply pressure to the relief tubing, and the amount of pressure applied to the relief tubing is based on measurement data from the detector.

9. The enteral feeding gastric pressure relief system of claim 1, further comprising a clip configured to maintain the multi-way connector in a position at or below a patient's stomach level.

10. The enteral feeding gastric pressure relief system of claim 1, further comprising a collection reservoir raising apparatus, the collection reservoir raising apparatus comprising: a support stand; a pulley connected to the support stand; and a cord connected to the collection reservoir, wherein the cord is configured to fit through the pulley and raise the collection reservoir.

11. The enteral feeding gastric pressure relief system of claim 1, further comprising a drain port connected to the collection reservoir.

12. The enteral feeding gastric pressure relief system of claim 1, wherein the fluid delivery tubing has a first length defined by a minimum length required to position the mufti-way connector at a patient stomach level when the feeding tube is providing fluid nutrient to a patient.

13. A method for providing gastric pressure relief during enteral feeding, wherein the enteral feeding is implemented using a feeding container that delivers fluid nutrient to a feeding tube via an administration tubing, the method comprising:
    providing a gastric pressure relief system, the gastric pressure relief system comprising the feeding container connected to the administration tubing; a relief tubing; a delivery tube including a fluid delivery tubing segment in fluid communication with the administration tubing and the relief tubing; a multi-way connector having a first arm, a second arm, and a third arm, wherein the first arm is connected to the relief tubing, the second arm is connected to the delivery tube, and the third arm is connected to the administration tubing; a collection reservoir in fluid communication with the relief tubing, wherein the collection reservoir includes a vent configured to allow gas to pass through in both directions and at least one chamber configured to collect reflux fluids from a patient's stomach via the relief tubing; and a check valve configured to permit flow in one direction from the administration tubing to either the relief tubing or the delivery tube;

intubating the feeding tube in a patient, wherein the feeding tube has a proximal end outside the patient's body;

measuring the approximate shortest distance between the feeding tube proximal end and a vertical plane at the level of the patient's stomach;

setting the length of the fluid delivery tubing segment to approximately the measured shortest distance;

coupling the fluid delivery tubing segment to the feeding tube and to the multi-way connector; and providing fluid nutrient to the patient.

\* \* \* \* \*